(12) United States Patent
Volloch et al.

(10) Patent No.: US 6,960,430 B2
(45) Date of Patent: Nov. 1, 2005

(54) SCREENING METHODS FOR COMPOUNDS USEFUL IN THE REGULATION OF CELL PROLIFERATION

(75) Inventors: Vladimir Z. Volloch, Brookline, MA (US); Michael Sherman, Newton, MA (US)

(73) Assignee: Phylogency, Inc., Columbus, OH (US)

( * ) Notice: Subject to any disclaimer, the term of this patent is extended or adjusted under 35 U.S.C. 154(b) by 0 days.

(21) Appl. No.: 10/132,556

(22) Filed: Apr. 25, 2002

(65) Prior Publication Data

US 2003/0082629 A1 May 1, 2003

Related U.S. Application Data

(63) Continuation of application No. 09/936,879, filed as application No. PCT/US00/07350 on Mar. 17, 2000.
(60) Provisional application No. 60/125,046, filed on Mar. 18, 1999.

(51) Int. Cl.[7] .................................................. C12Q 1/00
(52) U.S. Cl. .............................................................. 435/4
(58) Field of Search ............................................... 435/4

(56) References Cited

U.S. PATENT DOCUMENTS

| 5,096,815 A | 3/1992 | Ladner et al. |
| 5,198,346 A | 3/1993 | Ladner et al. |
| 5,223,409 A | 6/1993 | Ladner et al. |

FOREIGN PATENT DOCUMENTS

| WO | WO 88/09810 | 12/1988 |
| WO | WO 90/11364 | of 1990 |
| WO | WO 98/20242 | of 1993 |
| WO | WO 94/18318 | of 1994 |

OTHER PUBLICATIONS

Ehrhart et al. "Specific interaction between a subset of the p53 protein family and heat shock proteins hsp 72/hsc73 in a human osteosarcoma cell line", Oncogene 3 (5) : 595–603 (1988).*
Huang et al. "Association of Peroxisome Proliferator–activated Receptot and Hsp 72 ", J. Biological Chemistry 269 (11) : 8493–9 (1994).*
Struzbecher et al., "Characterization of Mutant p53–hsp72/73 Protein–Protein Complexes by Transient Expression in Monkey COS Cells" Molecular and Cellular Biology 8 (9) : 3740–47 (1988).*
Mosser et al., 1997 Use of a Dicistronic Expression Cassette Encoding the Green Fluorescent Protein for the Screening and Selection of Cells Expressing Inducible Gene Products, BioTechniques 22(1) 150–160.
Mosser et al., 1997 Role of the Human Heat Shock Protein hsp70 in Protection against Stress–Induced Apoptosis Mol Cellular Biol 17(9):5317–5327.

Meriin et al., (1998) Proteasome Inhibitors Activate Stress Kinases and Induce Hsp72, J Biol Chem 273(11) 6373–6379.
Choukroun et al., 1998 Role of the Stress–activated Protein Kinase in Endothelin–induced Cardiomyocyte Hypertryphy J Clin Invest 102(7) 1300–1320.
Li et al., 1992 Heat Shock Protein hsp70 protects cells from thermal stress even after deletion of its ATP–binding Domain, Proc Natl Acad Sci USA 89:2036–2040.
Houghten et al., 1991 Generation and Use of Synthetic Peptide Combinatorial Libraries for Basic Research and Drug Discovery, Nature 354:84–86.
Scott and Smith., 1990 Searching for Peptide Ligands with an Epitope Library, Science 249:386–390.
Langer 1990 New Methods of Drug Discovery, Science 249:1527–1533.
Tavaria, M. et al., 1996, *Cell Stress & Chaperones* 1:23–28.
Jaattela, M., 1992, *EMBO J*. 11:3507–3512.
Wei, Y., 1994, *Cancer Res.* 54:4952–4957.
Li et al., 1995, *Int. J. Hyperthermia* 11:459–488.
Ciocca et al., 1993, *Natl. Cancer Inst.* 85:570–574.
Jaattela, M. 1995, *Int. J. Cancer* 60:689–693.
Seo et al., 1996, *Biochem. Biophys. Res. Commun.* 218:582–587.
Kebers et al., 1998, *Experimental Cell Research* 240:197–205.
Janicke et al., 1998, *J. Biol. Chem.* 273:9357–9360.
Bursch et al., 1996, *Carcinogenesis* 17:1595–1607.
Wuerzberger et al., 1998, *Cancer Research* 58:1876–1885.
van England et al., 1996, *Cytometry* 24:131–139.
Sherwood et al., *Methods in Cell Biology* 46:77–97.
Fodor et al., 1991, *Science* 251:767–773.
Lam et al., 1991, *Nature* 354: 82–84.
Medynski, 1994, *Bio/Technology* 12:709–710.
Gallop et al., 1994, *J. Medicinal Chemistry* 37(9):1233–1251.
Ohlmeyer et al., 1993, *Proc. Natl. Acad. Sci. USA* 90:10922–10926.
Erb et al., 1994, *Proc. Natl. Acad. Sci. USA* 91:11422–11426.
Houghton et al.1992, *Biotechniques* 13:412.
Jayawickreme et al., 1994, *Proc. Natl. Acad. Sci USA* 91:1614–1618.
Salmon et al., 1993, *Proc. Natl. Acad. Sci USA* 90:11708–11712.

(Continued)

Primary Examiner—Sandra E. Saucier
(74) Attorney, Agent, or Firm—Baker Botts LLP

(57) ABSTRACT

The present invention relates to drug screening assays and methods for the treatment of proliferative disorders associated with elevated levels of heat shock protein 72 (Hsp72) expression in a cell. The invention is based on the discovery that overexpression of full length Hsp72 protein, or the C-terminal protein binding domain of Hsp72, results in oncogenic transformation of cells.

5 Claims, 26 Drawing Sheets

OTHER PUBLICATIONS

Figure 1A:
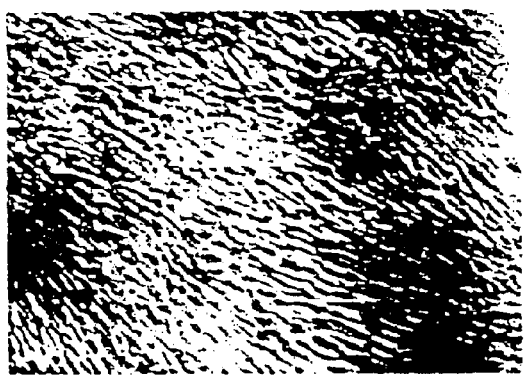

Brenner and Lerner, 1992, *Proc. Natl. Acad Sci. USA* 89:5381–5383.
Scott and Smith, 1990, *Science*, 249:386–390.
Devlin et al., 1990, *Science*, 249:404–406.
Christian, R.B., et al., 1992, *J. Mol. Biol.* 227:711–718.
Lenstra, 1992, *J. Immunol. Meth.* 152:149–157.
Simon et al. 1992, *Proc. Natl. Acad. Sci. USA* 89:9367–9371.
Ostresh et al., 1994, *Proc. Natl. Acad. Sci. USA* 91:11138–11142.
Parmley and Smith, 1989, *Adv. Exp. Med. Biol* 215–218.
Fowlkes et al., 1992; *BioTechniques* 13:422–427.
Oldenburg et al., 1992, *Proc. Natl. Acad. Sci. USA* 89:5393–5397.
Yu et al., 1994, *Cell* 76:933–945.
Staudt et al., 1988, *Science* 241:577–580.
Brock et al., 1992, *Nature* 355:564–566.
Tuerk et al., 1992, *Proc. Natl. Acad. Sci USA* 89:6988–6992.
Ellington et al., 1992, *Nature* 355:850–852.
Rebar and Pabo, 1993, *Science* 263:671–673.
Fields and Song, 1989, *Nature* 340:245–246.
Chien et al., 1991, *Proc. Natl. Acad. Sci. USA* 88:9578–9582 p. 16.
Meriin et al. (1999, *Mol. Cel. Biol.*) p. 18.
Letsinger et al., 1989, *Proc. Natl. Acad. Sci. USA* 86:6553–6556.
Lemaitre et al., 1987, *Proc. Natl. Acad. Sci.* 84:648–652.
Krol et al. 1 1988; *Bio Techniques* 6:958–976.
Zon, 1988, *Pharm. Res.* 5:539–549.
Gautier et al., 1987, *Nucl. Acids Res.* 15:6625–6641.
Stein et al. 1988, *Nucl. Acids Res.* 16:3209.
Sarin et al., 1988, *Proc. Natl. Acad. Sci. USA* 85:7448–7451.
Sarver et al. 1990, *Science* 247:1222–1225.
Inoue et al., 1987, *Nucl. Acids. Res.* 15:6131–6148.
Inoue et al., 1987, *FEBS Lett.* 215:327–330.
Bernoist and Chambon, 1981, *Nature* 290:304–310.
Yamamoto et al., 1980, *Cell* 22:787797.
Wagner et al., 1981, *Proc. Natl. Acad. Sci. USA* 78:1441–1445.
Brinster et al., 1982, *Nature* 296:39–42.
Leonetti et al., 1990, *Proc. Natl. Acad. Sci. USA* 87:2448–2451.
Renneisen et al., 1990, *J. Biol. Chem.* 265:16337–16342.
Kohler and Milstein (1975) *Nature* 256:495–497.
Kozber et al., 1983, *Ummunology Today* 4:2.
Cole et al., 1985 in *Moleclonal Antibodies and Cancer Therapy*, Alan R. Liss, Inc., pp. 77–96.
Hust et al., 1989 *Science* 246:12751281.
Robbins and Angell, 1976, *Basic Pathology*, 2d Ed., W.B. Saunders Co., Philadelphia, pp. 68–79.
Wu and Wu, 1987, *J. Biol. Chem.* 262:4429–4432.
Treat et al., in *Liposomes in the Therapy of Infectious Disease and Cancer*, Lopez–Berestein and Fidler (eds.), Liss, New York, pp. 353–365 (1989).
Lopez–Berestein, *ibid.*, pp. 317–327.
Langer, *supra*; Sefton, CRC *Crit. Ref. Biomed. Eng.* 14:201 (1987).
Buchwald et al., *Surgery* 88:507 (1980).
Saudek et al., *N. Engl. J. Med.* 321:574 (1989).
Langer and Peppas, *J. Macromol. Sci Rev. Macromol. Chem* 23:61 (1983).
Levy et al., *Science* 228:190 (1985).
During et al., *Ann. Neurol* 25:351 (1989).
Howard et al., *J. Neurosurg.* 71:105 (1989).
Goodson, in *Medical Applications of Controlled Release*, *supra*, vol. 2, pp. 115–138 (1984).
Li et al., 1992, *Proc. Natl. Acad. Sci. USA* 89:2036–2040.
Mosser et al., 1997a, *Mol. Cell Biol* 17:5317–5327.
Mosser et al., 1997b, *Biotechniques* 22:150–161.
Jani et al., 1997, *J. Virol. Methods* 64:111–124.
Heydari et al., 1994, *Experientia* 50:1092–1098.
Rattan, S. 1996, *Exp. Gerontol* 31:33–47.
Volloch, V., et al., 1998, *Cell Stress 7 Chaperones* 3:264–271.
Massie, B. et al., 1998, *J. Virology* 72(3):2289–2296.
Choukroun, G. et al., (1998), *J. Clin. Invest.* 102:1311–1320.
Buzzard, K.A., et al., 1998, *J. Biol. Chem.* 273:17147–17153.
Zanke, B.W., et al. 1996, *Current Biology* 6(5):606–613.
Verhaij, M. et al., 1996 *Nature* 380(6569):75–79.
Sanchez, I. Hughes et al., 1994, *Nature* 372(6508):794–798.
Chen Y.R. et al., 1996, *J. Biol. Chem.* 271(50):31929–31936.
Ganiatsas, S. et al., 1998, *Proc. Natl. Acad. Sci USA* 95:6881–6886.
Finch, a. et al., 1997, *Febs. Lett.* 418:144–14.

\* cited by examiner

Rat-1  MVH

← Hsp72

Rat-1  ● ← c-Jun

MVH  ● ← c-Jun

C  HS

Rat-1    ← p-JNK2
         ← p-JNK1

MVH      ← p-JNK2
         ← p-JNK1

C  HS

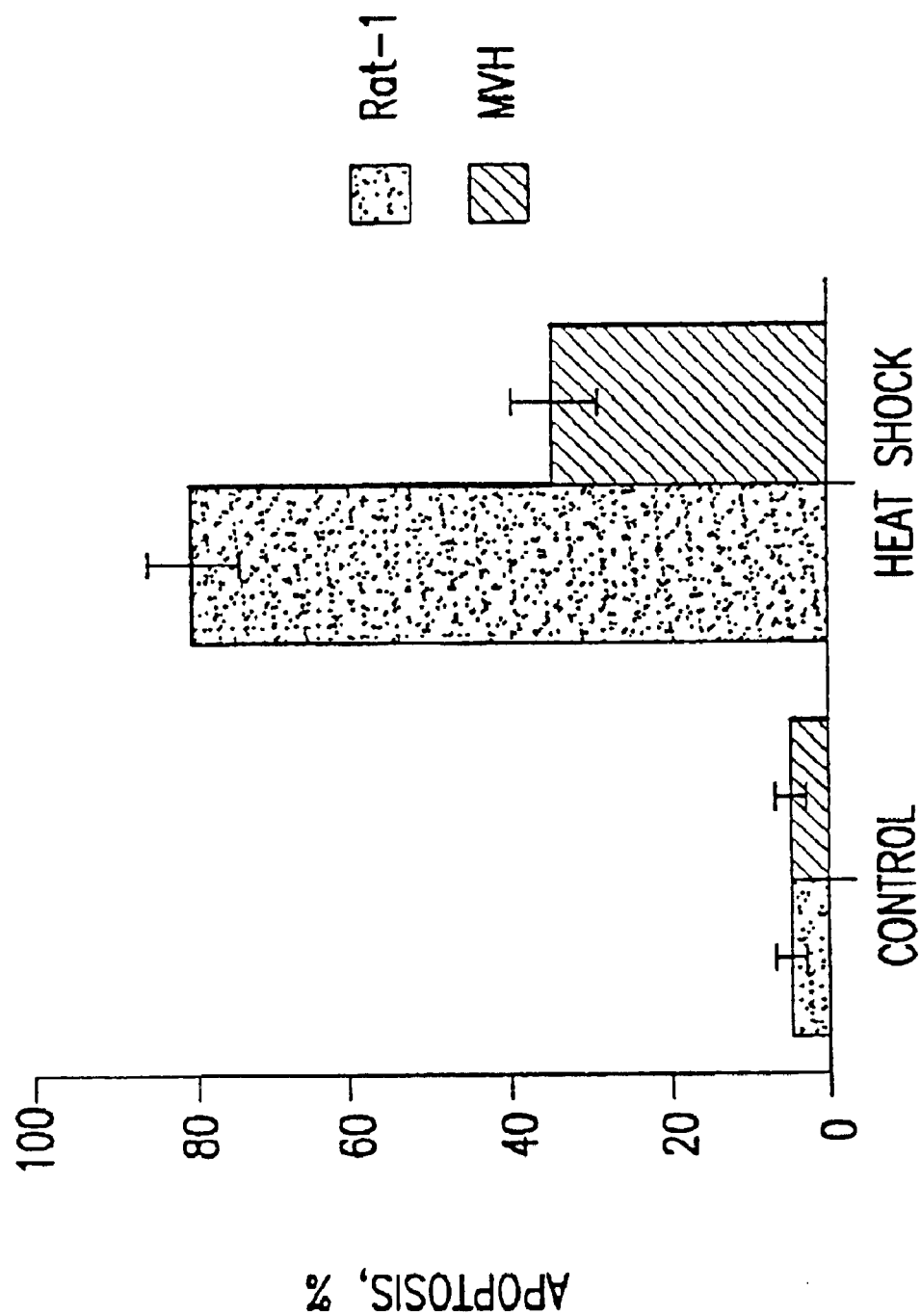

BASE COUNT   601 a    780 c    834 g    485 t
ORIGIN Chromosome 6p21.3.
```
   1 cgccatggag accaacaccc ttcccaccgc cactccccct tcctctcagg gtccctgtcc
  61 cctccagtga atcccagaag actctggaga gttctgagca ggggcggca ctctggcctc
 121 tgattggtcc aaggaaggct gggggcagg acgggaggcg aaaccctgg aatattcccg
 181 acctggcagc ctcatcgagc tcggtgattg gctcagaagg gaaaaggcgg gtctccgtga
 241 cgacttataa aacgccaggg gcaagcggtc cggataacgg ctagcctgag gagctgctgc
 301 gacagtccac tacctttttc gagagtgact cccgttgtcc caaggcttcc cagagcgaac
 361 ctgtgcggct gcaggcaccg gcgcgtcgag tttccggcgt ccggaaggac cgagctcttc
 421 tcgcggatcc agtgttccgt ttccagcccc caatctcaga gcggagccga cagagagcag
 481 ggaaccggca tggccaaagc cgcggcgatc ggcatcgacc tgggcaccac ctactcctgc
 541 gtgggggtgt tccaacacgg caaggtggag atcatcgcca acgaccaggg caaccgcacc
 601 accccagct acgtggcctt cacggacacc gagcggctca tcggggatgc ggccaagaac
 661 caggtggcgc tgaacccgca gaacaccgtg tttgacgcga agcgcctgat tggccgcaag
 721 ttcggcgacc cggtggtgca gtcggacatg aagcactggc ctttccaggt gatcaacgac
 781 ggagacaagc ccaaggtgca ggtgagctac aaggggggaga ccaaggcatt ctaccccgag
 841 gagatctcgt ccatggtgct gaccaagatg aaggagatcg ccgaggcgta cctgggctac
 901 ccggtgacca acgcggtgat caccgtgccg gcctacttca acgactcgca gcgccaggcc 961 accaaggatg cgggtgtgat cgcggggctc aacgtgctgc ggatcatcaa cgagcccacg
1021 gccgccgcca tcgcctacgg cctggacaga acgggcaagg gggagcgcaa cgtgctcatc
1081 tttgacctgg gcgggggcac cttcgacgtg tccatcctga cgatcgacga cggcatcttc
1141 gaggtgaagg ccacggccgg ggacacccac ctgggtgggg aggactttga acaggctg
1201 gtgaaccact tcgtggagga gttcaagaga aaacacaaga aggacatcag ccagaacaag
1261 cgagccgtga ggcggctgcg caccgcctgc gagagggcca agaggaccct gtcgtccagc
1321 acccaggcca gcctggagat cgactccctg tttgagggca tcgacttcta cacgtccatc
1381 accagggcga ggttcgagga gctgtgctcc gacctgttcc gaagcaccct ggagcccgtg
1441 gagaaggctc tgcgcgacgc caagctggac aaggcccaga ttcacgacct ggtcctggtc
1501 gggggctcca cccgcatccc caaggtgcag aagctgctgc aggacttctt caacgggcgc
1561 gacctgaaca agagcatcaa ccccgacgag gctgtggcct acgggcggc ggtgcaggcg
1621 gccatcctga tggggacaa gtccgagaac gtgcaggacc tgctgctgct ggacgtggct
1681 cccctgtcgc tggggctgga gacggccgga ggcgtgatga ctgccctgat caagcgcaac
1741 tccaccatcc ccaccaagca gacgcagatc ttcaccacct actccgacaa ccaacccggg
1801 gtgctgatcc aggtgtacga gggcgagagg gccatgacga aagacaacaa tctgttgggg
1861 cgcttcgagc tgagcggcat ccctccggcc cccaggggcg tgccccagat cgaggtgacc
1921 ttcgacatcg atgccaacgg catcctgaac gtcacggcca cggacaagag caccggcaag
1981 gccaacaaga tcaccatcac caacgacaag ggccgcctga gcaaggagga gatcgagcgc
2041 atggtgcagg aggcggagaa gtacaaagcg gaggacgagg tgcagcgcga gagggtgtca
2101 gccaagaacg ccctggagtc ctacgccttc aacatgaaga gcgccgtgga ggatgagggg
2161 ctcaagggca agatcagcga ggccgacaag aagaaggtgc tggacaagtg tcaagaggtc
2221 atctcgtggc tggacgccaa caccttggcc gagaaggacg agttgagca caagaggaag
2281 gagctggagc aggtgtgtaa ccccatcatc agcggactgt accagggtgc cggtggtccc
2341 gggcctgggg gcttcgggc tcagggtccc aagggagggt ctgggtcagg ccccaccatt
2401 gaggaggtag attaggggcc tttccaagat tgctgttttt gttttggagc ttcaagactt
2461 tgcatttcct agtatttctg tttgtcagtt ctcaatttcc tgtgtttgca atgttgaaat
2521 ttttggtga agtactgaac ttgcctttt ttccggtttc tacatgcaga gatgaattta
2581 tactgccatc ttacgactat ttcttctttt taatacactt aactcaggcc atttttaag
2641 ttggttactt caaagtaaat aaactttaaa attcaagtga tgcccttta ttcctttatt
```

FIG.16A

```
/translation="MAKAAAIGIDLGTTYSCVGVFQHGKVEIIANDQGNRTTPSYVAF
TDTERLIGDAAKNQVALNPQNTVFDAKRLIGRKFGDPVVQSDMKHWPFQVINDGDKPK
VQVSYKGETKAFYPEEISSMVLTKMKEIAEAYLGYPVTNAVITVPAYFNDSQRQATKD
AGVIAGLNVLRIINEPTAAAIAYGLDRTGKGERNVLIFDLGGGTFDVSILTIDDGIFE
VKATAGDTHLGGEDFDNRLVNHFVEEFKRKHKKDISQNKRAVRRLRTACERAKRTLSS
STQASLEIDSLFEGIDFYTSITRARFEELCSDLFRSTLEPVEKALRDAKLDKAQIHDL
VLVGGSTRIPKVQKLLQDFFNGRDLNKSINPDEAVAYGAAVQAAILMGDKSENVQDLL
LLDVAPLSLGLETAGGVMTALIKRNSTIPTKQTQIFTTYSDNQPGVLIQVYEGERAMT
KDNNLLGRFELSGIPPAPRGVPQIEVTFDIDANGILNVTATDKSTGKANKITITNDKG
RLSKEEIERMVQEAEKYKAEDEVQRERVSAKNALESYAFNMKSAVEDEGLKGKISEAD
KKKVLDKCQEVISWLDANTLAEKDEFEHKRKELEQVCNPIISGLYQGAGGPGPGGFGA
```

FIG. 16B

SCREENING METHODS FOR COMPOUNDS USEFUL IN THE REGULATION OF CELL PROLIFERATION

This application is a Continuation of application Ser. No. 09/936,879 filed Oct. 1, 2003. This application is based upon: prior application No.: PCTUS00/07350 filed Mar. 17, 2000, incorporated by reference herein, Provisional application Ser. No. 60/125,046.

1. INTRODUCTION

The present invention relates to drug screening assays and methods for the treatment of proliferative disorders associated with elevated levels of heat shock protein 72 (Hsp72) expression in a cell. The invention is based on the discovery that overexpression of full length Hsp72 protein, or the C-terminal protein binding domain of Hsp72, results in oncogenic transformation of cells.

2. BACKGROUND OF INVENTION

Cells respond to heat and other environmental stresses by expressing inducible heat shock proteins. The most prominent and best characterized of the stress proteins is the Hsp70 family of proteins which encompasses a group of at least eleven highly related proteins, the major protein of which, in humans, is designated Hsp72.

The various Hsp70 isoforms are encoded by a multigene family of genes. The Hsp70 proteins are highly conserved ATP binding proteins present in all cell types and distributed throughout all cellular compartments. Hsp70 and the chaperone protein DnaI function together in a complex to carry out a number of biochemical activities. Such activities include nascent protein folding, protein translocation across the endoplasmic reticulum, and prevention of protein aggregation. The heat shock proteins also associate with denatured or partially unfolded proteins, protecting them from further denaturation and assisting in their refolding. (Tavaria, M. et al., 1996, Cell Stress & Chaperones 1:23–28). The release of "processed" proteins is mediated by ATP.

Hsp70 has been shown to intervene in the apoptotic process. For example, the transfection of the Hsp70 gene into cells protects those cells from cell death induced by TNF-α (Jaattela, M., 1992, EMBO J. 11:3507–3512). Furthermore, pretreatment of tumor cells with Hsp70 antisense oligomer enhanced quercetin-induced apoptosis (Wei, Y., 1994, Cancer Res. 54:4952–4957).

Levels of Hsp72 have been demonstrated to be increased in the majority of tumor cells (Li et al., 1995, Int. J. Hyperthermia 11:459–488). In some instances, such as breast cancer, the level of Hsp72 serves as a positive prognostic marker, and, in some patients, the only independent predictor of disease reoccurrence (Ciocca et al., 1993, Natl. Cancer Inst. 85:570–574). In addition, overexpression of Hsp70 in mouse fibrosarcoma cells (WEHI-S) conferred tumorigenicity in syngenic mice (Jaattela, M., 1995, Int. J. Cancer 60:689–693). In transgenic mice, constitutive expression of Hsp72 in T lymphocytes coincides with a greatly increased incidence of generalized malignant lymphoma (Seo et al., 1996, Biochem. Biophys. Res. Commun. 218:582–587).

3. SUMMARY OF THE INVENTION

The present invention relates to methods for identifying compounds capable of modulating the expression of the Hsp72 gene and/or the synthesis or activity of the Hsp72 gene product. It is based, at least in part, on the identification of an association between overexpression of Hsp72 and oncogenic transformation.

The invention further relates to methods for treatment of Hsp72-mediated proliferative disorders, wherein said methods comprise administering a compound which modulates the expression of the Hsp72 gene and/or the synthesis or activity of the Hsp72 gene product so that symptoms of the proliferative disorder are ameliorated.

4. BRIEF DESCRIPTION OF THE DRAWINGS

FIGS. 1A–D. Effect of constitutive expression of Hsp72 on foci formation, anchorage-independent growth and tumorogenicity of Rat-1 cells. (FIG. 1A) Rat-1 cells stably transfected with vector alone (recloned MV6 cells, Li et al, 1992). (FIG. 1B) Rat-1 cells stably transfected with vector containing human Hsp72 gene (Li et al, 1992) (FIG. 1C) Cells constitutively expressing Hsp72 are able to grow in an anchorage-independent manner. MVH cells in soft agar three weeks after plating. No colonies were seen with MV6 cells. Picture was taken at 100× magnification. (FIG. 1D) Cells constitutively expressing Hsp72 form tumors in mice. Nude mice four weeks after injection of $10^5$ (left anterior) or $10^6$ (right anterior) MVH cells. Tumors indicated by arrows. When the same quantities of MV6 cells were injected into left and right posterior of the same mice, no tumors were seen.

Figure 2:

FIG. 2. Expression of Hsp72 or its C-terminal peptide binding domain (C-terminal fragment, CTF) in stably transfected or infected Rat-1 cells. Immunoblots of cell proteins with either SPA810 antibody specific for Hsp72 (lanes 1–4) or SPA820 antibody which recognizes CTF (lanes 5,6). Lanes 1 and 5: MV6 cells; Lane 2: MVH cells; Lane 3: Rat-1 cells infected with adenoviruses containing Hsp72 and tTA and maintained in the presence of 50 nM anhydrotetracycline. Lane 4: Rat-1 cells infected with adenoviruses containing Hsp72 and tTA in the absence of tetracycline. Lane 6: Rat-1 cells stably transfected with CTF-containing vector (MVHΔBg cells, Li et al, 1992).

Figure 3C:
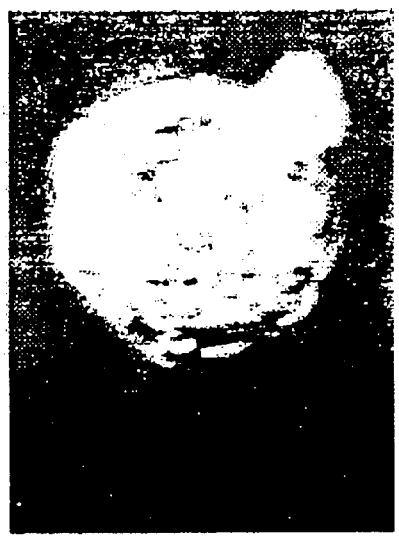
Figure 3B:
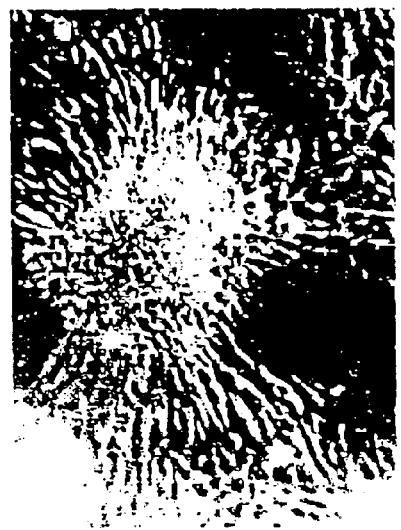
Figure 3A:

FIGS. 3A–C. Effect of regulated expression of Hsp72 on foci formation and anchorage-independent growth of Rat-1 cells. (FIG. 3A) Rat-1 cells were infected with Hsp72-containing adenovirus and maintained in the presence of tetracycline. (FIG. 3B) Rat-1 cells were infected with Hsp72-containing adenovirus and maintained in the absence of tetracycline. (FIG. 3C) Cells expressing Hsp72 from adenoviral vector form colonies in soft agar. Rat-1 cells infected with Hsp72-containing adenovirus in the absence of tetracycline in soft agar ten days after plating. Picture was taken at 200× magnification. No colonies were seen in the presence of tetracycline.

Figure 4C:
Figure 4B:
Figure 4A:
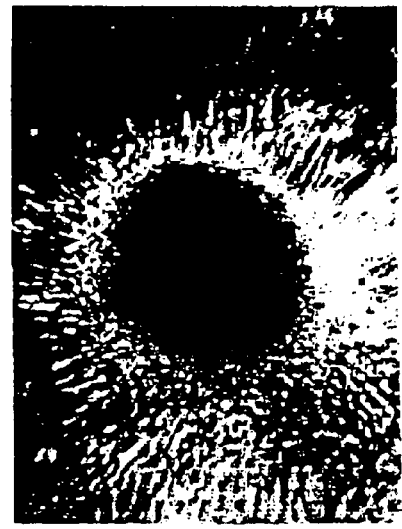

FIGS. 4A–C. Effect of constitutive expression of CTF on foci formation, anchorage-independent growth and tumorogenicity of Rat-1 cells. (FIG. 4A) Loss of contact inhibition in cells constitutively expressing CTF. MVHΔBg cells stably transfected with CTF-containing vector. (FIG. 4B) Cells constitutively expressing CTF are able to grow in an anchorage-independent manner. MVHΔBg cells in soft agar three weeks after plating. Picture was taken at 100× magnification. (FIG. 4C) Cells constitutively expressing CTF form tumors in mice. Nude mice four weeks after injection of $10^5$ (left anterior) or $10^6$ (right anterior) MVHΔBg cells, tumors indicated by arrows. The same quantities of control cells were injected into left and right posterior of the same mice, no tumors were seen.

FIGS. 5A–D Comparison of colonies formed in soft agar by Hsp72-transfected, Hsp72-infected, and CTF-transfected cells. Identical number of MV6 cells, MVH cells, and Hsp72-infected Rat-1 cells were plated in soft agar and incubated for twelve days. Pictures were taken at 25× magnification. (FIG. 5A) Control MV6 cells in soft agar. (FIG. 5B) MVH cells in soft agar. (FIG. 5C) Rat-1 cells infected with adenoviruses containing Hsp72 and rTA in the absence of tetracycline in soft agar. (FIG. 5D) MVHΔBg cells in soft agar.

Figures 6A, 6C, 6D:
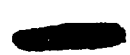

FIGS. 6A–D. Constitutive expression of Hsp72 in Rat-1 fibroblasts suppresses heat-induced apoptosis but does not inhibit JNK activation. Rat-1 cells and Hsp72-expressing variant (MVH) were subjected to heat shock (45° C., 50 min) and their apoptosis and JNK activity were measured as described in Materials and Methods. (FIG. 6A) Levels of Hsp72 in Rat-1 and MVH cells; (FIG. 6B) heat-induced apoptosis in Rat-1 and MVH cells; (C,D) heat-induced JNK activity (FIG. 6C) and phosphorylation (FIG. 6D) in Rat-1 and MVH cells. Apoptosis (mean+/–SD) was assessed 24 h after heat shock by Hoechst staining; JNK activity after heat shock was assessed by c-jun phosphorylation (FIG. 6C) and Ab to phosphorylated (active) JNK (FIG. 6D)

Figure 7:
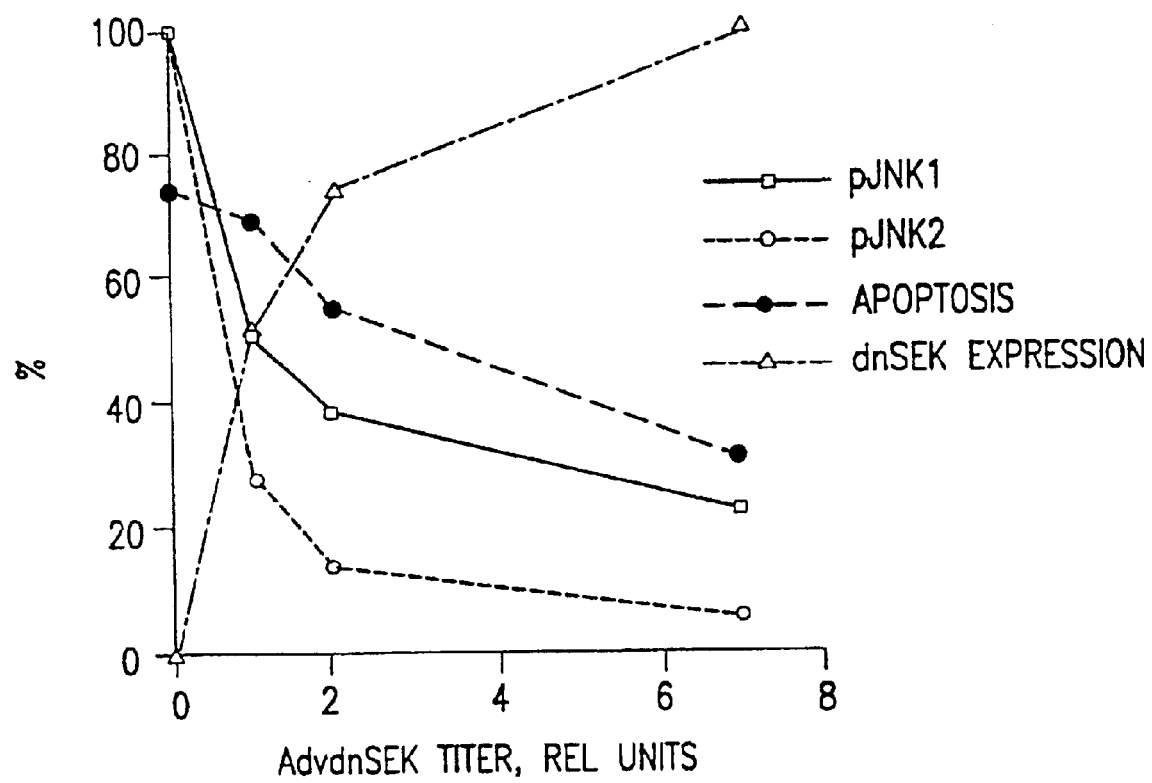

FIG. 7. Inhibition of JNK activation suppresses heat-induced apoptosis of Rat-1 cells. Rat-1 cells were infected with increasing titers of adenovirus expressing dominant-negative SEK (SEK K/R), and activation of JNK1, JNK2 and apoptosis after heat shock (45° C., 50 min) were assessed as described in Legend to FIG. 1. Expression of SEK(K/R) was quantified with antibody to SEK. One relative unit of SEK(K/R) adenovirus was $10^9$ particles per 35 mm dish. Activation of JNK and apoptosis were measured as described in Materials and Methods. Percent of effects in control cells is plotted on the ordinate axis.

Figure 8A:
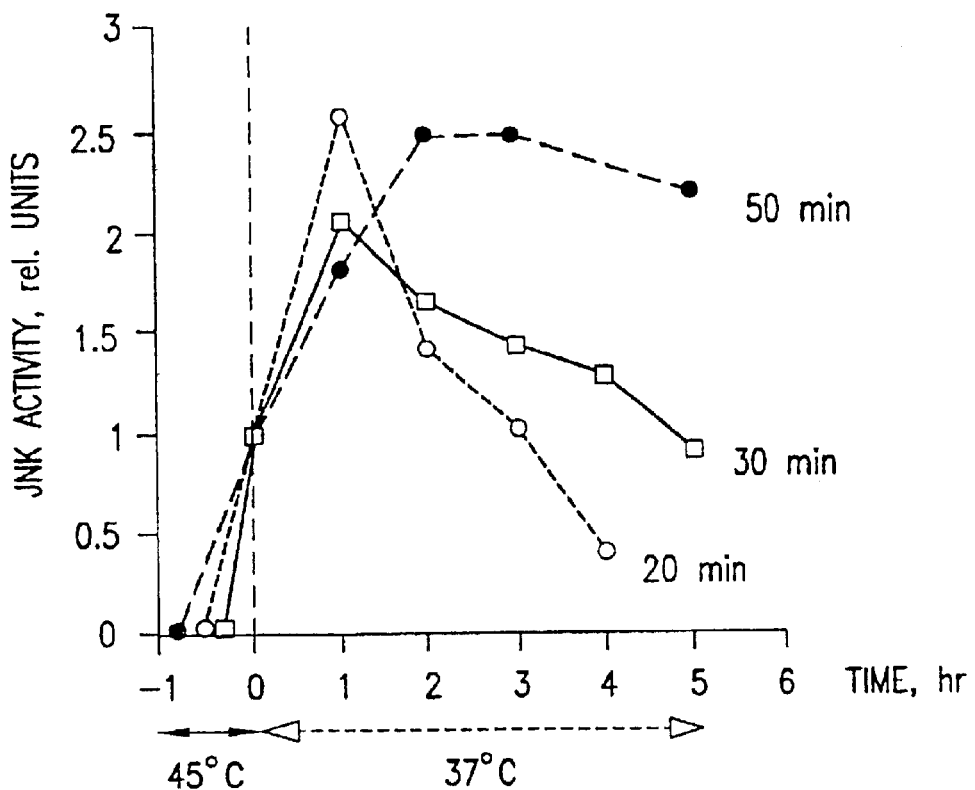
Figure 8B:
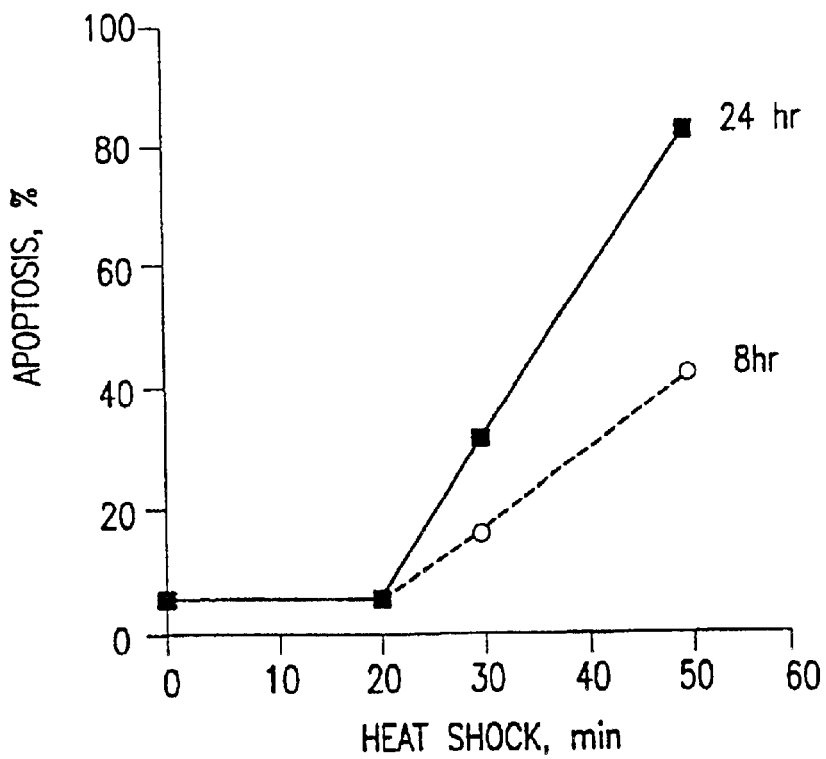

FIGS. 8A–B. Heat-induced apoptosis in Rat-1 cells correlates with duration of JNK activation. Rat-1 cells were subjected to various heat shock treatments (20, 30 or 50 min at 45° C.), then transferred to normal temperature (37° C.) and their JNK activity (FIG. 8A) and apoptosis (FIG. 8B) were measured at the indicated time points. JNK activity immediately after heat shock was the same under various treatments and was taken as one relative unit.

Figure 9A:
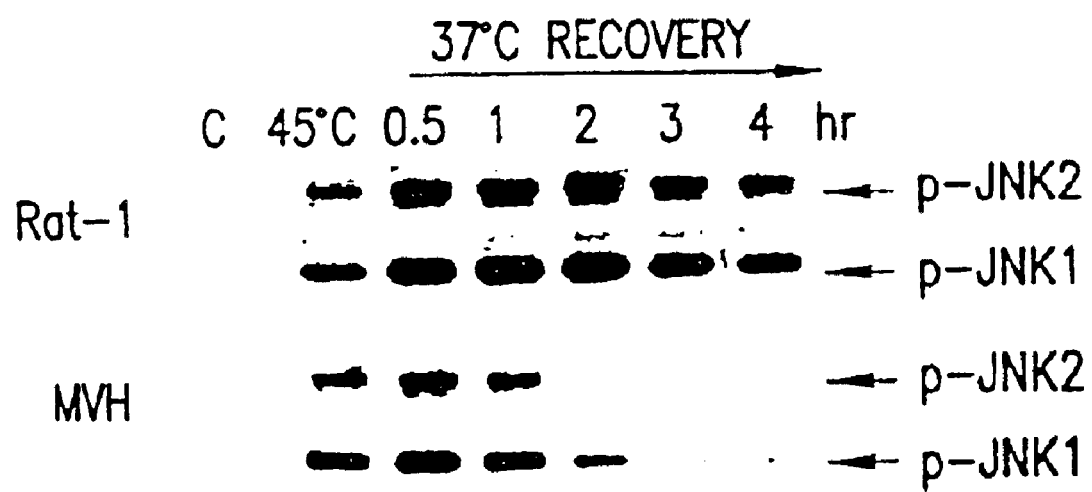
Figure 9B:
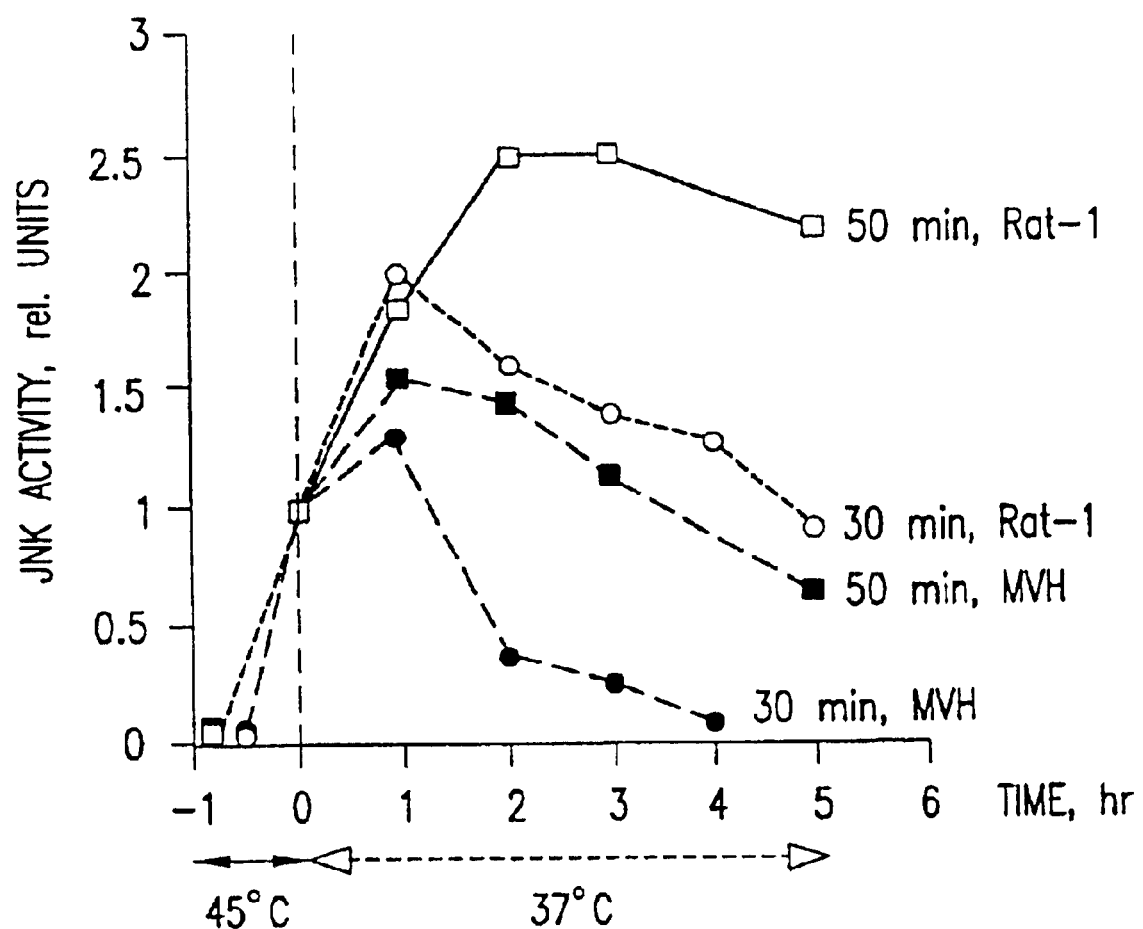

FIGS. 9A–B. Constitutive Hsp72 expression in Rat-1 cells accelerates JNK inactivation after heat shock. Rat-1 cells and their Hsp72-expressing variant (MVH) were subjected to heat shock and JNK activity were measured immediately after heat shock (45 ° C.) and after recovery at 37° C. (FIG. 9A) JNK1 and JNK2 activity (phosphorylation) after heat shock at 45° C. for 30 min; (FIG. 9B) Assessment of JNTK1 activity after heat shock at 45° C. for 30 min or 50 min. JNK activity immediately after heat shock was the same under various treatments and was taken as one relative unit.

Figure 10A:
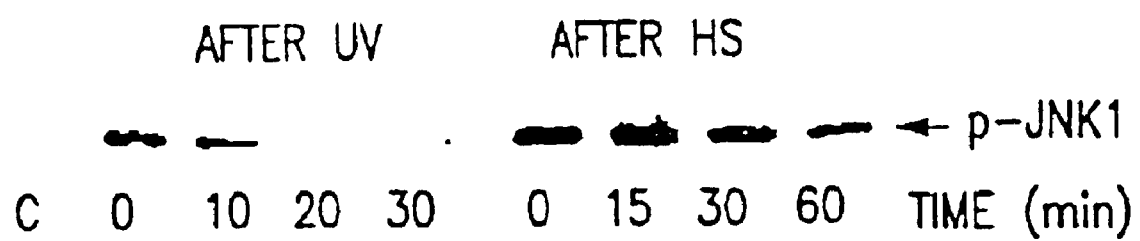
Figure 10B:
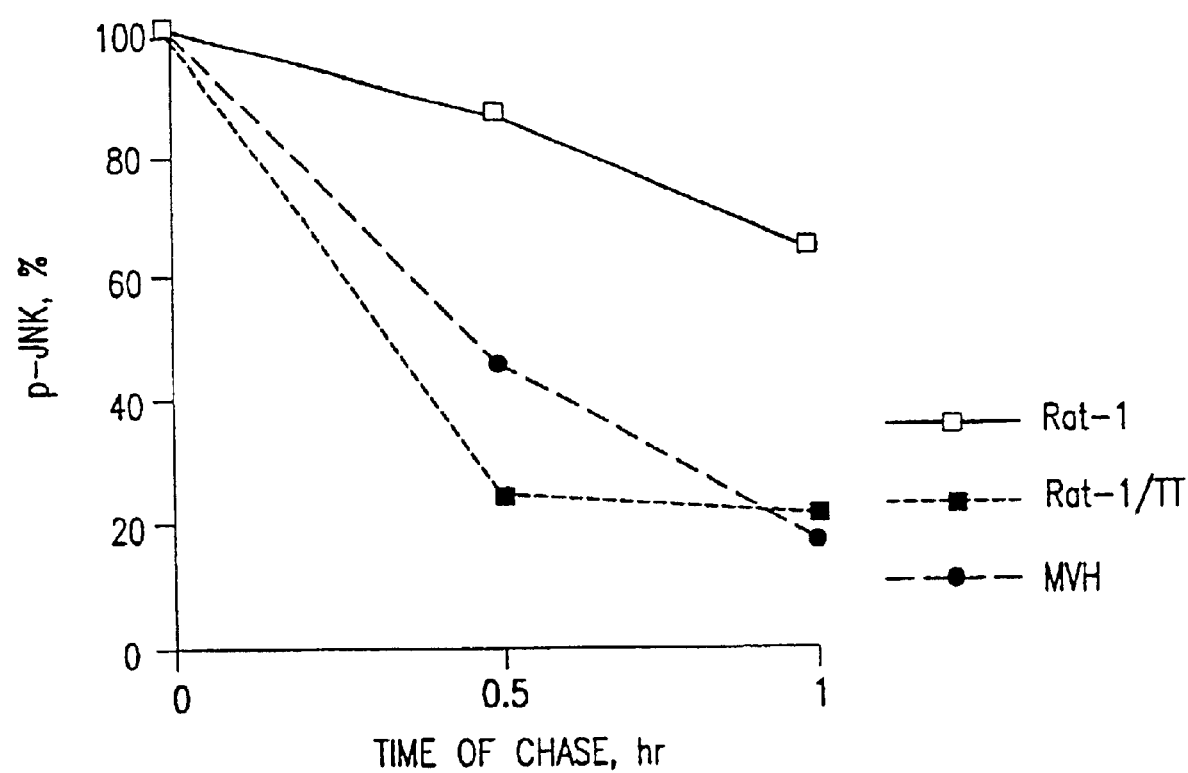

FIGS. 10A–B. Hsp72 expression alleviates heat-induced JNK phosphatase inactivation after heat shock in Rat-1 cells. (FIGS. 10A) heat shock inactivates JNK phosphatase in Rat-1 cells. Rat-1 cells were subjected to UV irradiation (400 J/m$^2$) or heat shock (45° C., 30 min) and JNK1 dephosphorylation was measured under ATP-depletion conditions (chase) at the indicated time points. Under the chase condition JNK phosphorylation by upstream kinases was totally suppressed, therefore the rate of JNK dephosphorylation reflects JNK phosphatase activity. (FIG. 10B) JNK phosphatase activity after heat shock is increased in Hsp72-expressing cells. Cells were subjected to heat shock (45° C., 30 min) following 2 hr of recovery at 37° C., and JNK1 dephosphorylation was measured under the chase conditions (see above). Rat-1-control cells; MVH—Hsp72 expressing variant; Rat-1/TT-thermotolerant Rat-1 (cells exposed to mild heat treatment at 45° C. for 15 with recovery at 37° C. for 16 hr prior to heat shock at 45° C. for 30 min).

Figure 11A:
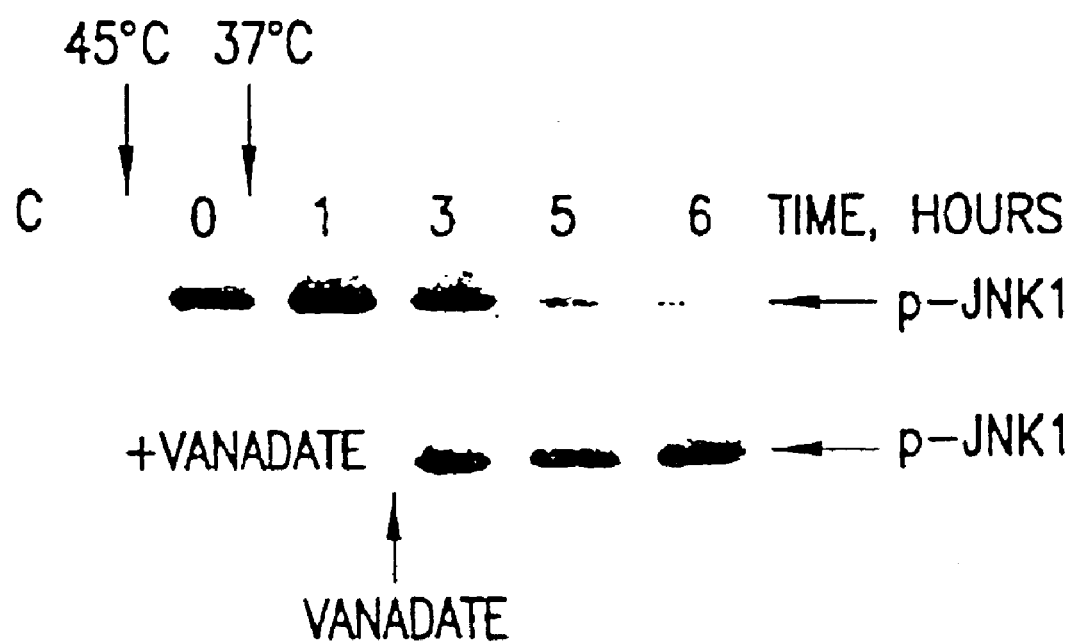
Figure 11B:
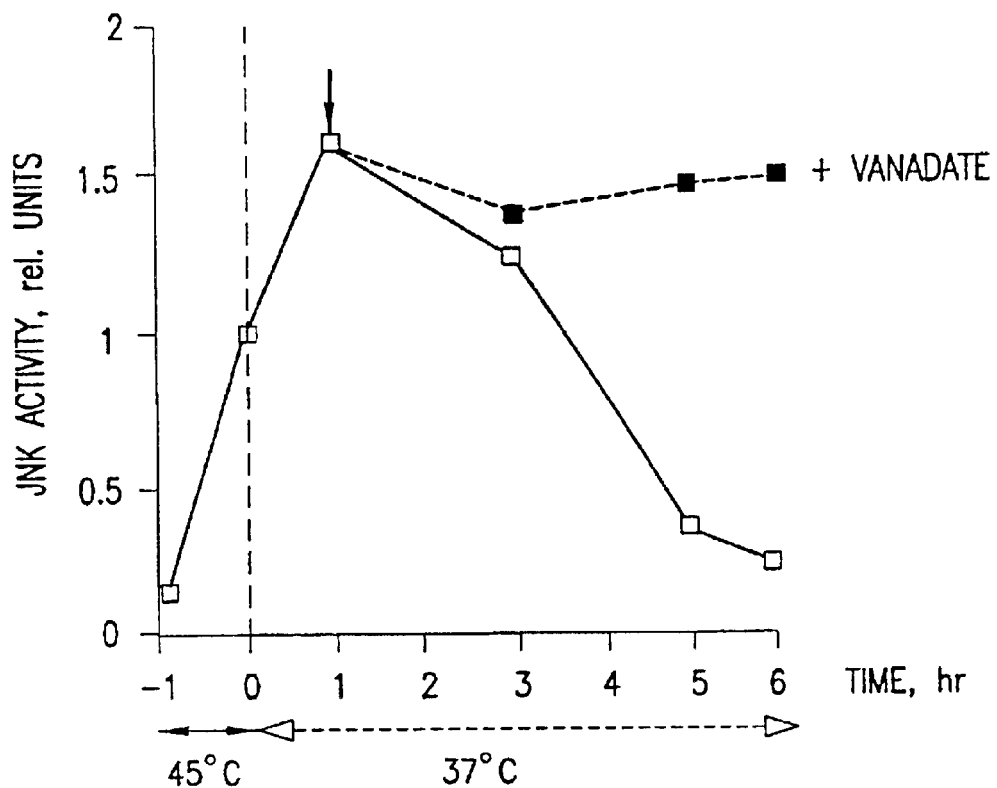
Figure 11C:
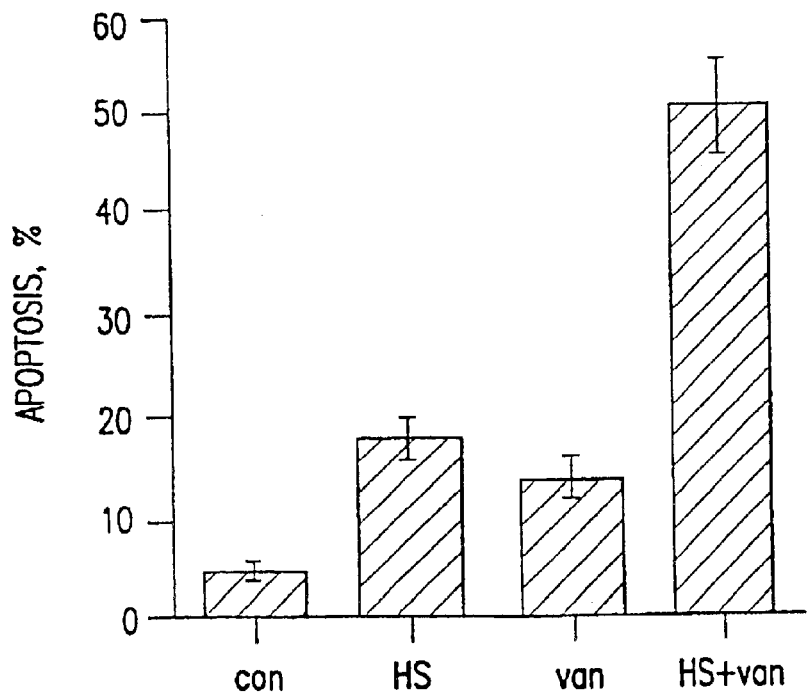

FIGS. 11A–C. Inhibition of JNK dephosphorylation in Hsp72-expressing cells by vanadate abolishes their thermoresistance. (FIG. 11A) Ortho-vanadate inhibits JNK dephosphorylation in Hsp72-expressing (MVH) cells. The cells were subjected to heat shock (45° C., 50 min) and then transferred to normal temperature (37° C.). After 1 hr of incubation at 37° C., ortho-vanadate (0.5 mM) was added to a portion of the cells, while other portion was left without the drug, and JNK1 activity was measured by antibody to phospho-JNK. Ortho-vanadate itself had no significant effect on JNK activity. (FIG. 11B) Quantitation of data in FIG. 11A. (FIG. 11C) Ortho-vanadate abolishes thermoresistance of Hsp72-expressing cells. The cells were treated as described above, and their apoptosis (mean+/–SD) was assessed 7 hr after the treatments with heat shock (HS, 45° C., 50 min), orthovanadate (van, 0.5 mM), or their combination (HS+van).

Figure 12:
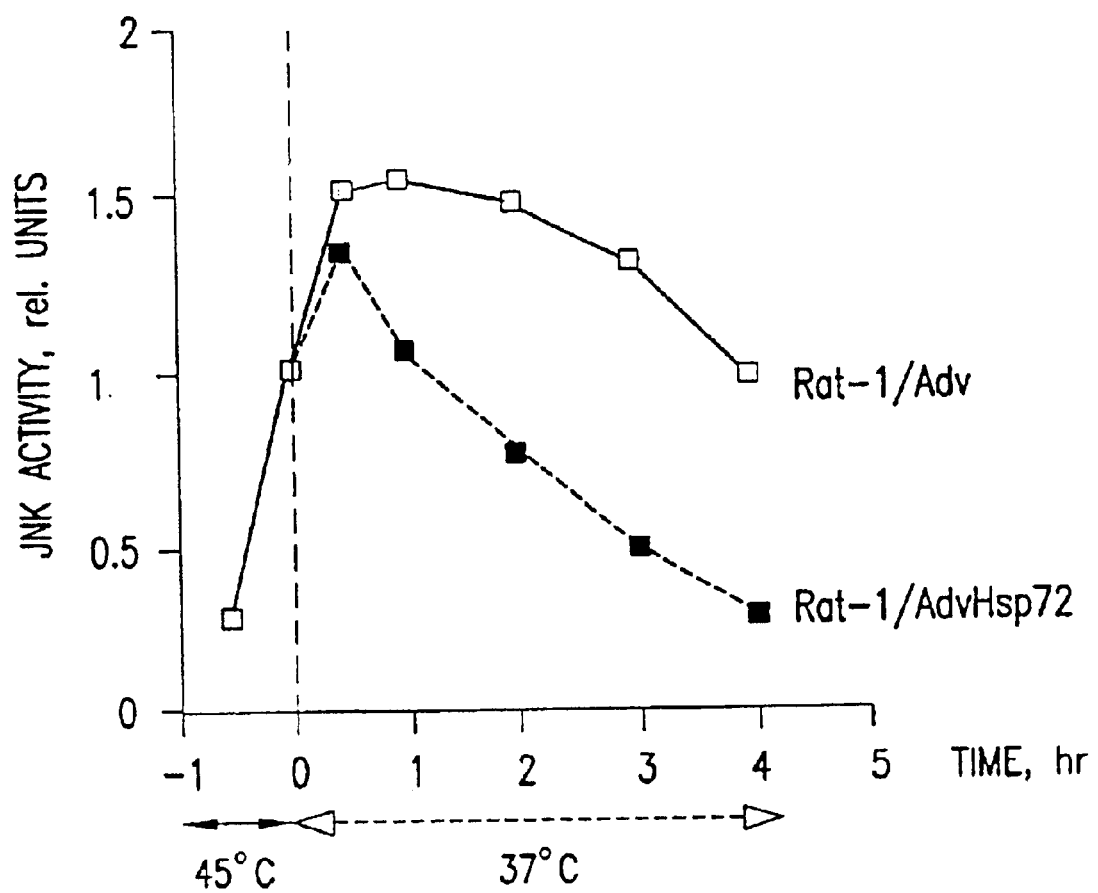

FIG. 12. Transient expression of Hsp72 in Rat-1 cells accelerates JNK inactivation after heat shock. Rat-1 cells were infected with a recombinant adenovirus vectors expressing Hsp72 under control of tetracycline-regulated transactivator protein tTA and incubated for 36 h in the presence or absence of tetracycline. Then Hsp72-expressing (Adv Hsp72) and mock-infected cells (Adv) were subjected to heat shock (45° C., 30 min) and JNK1 activity was assessed by immunoblot at the indicated time points. High level of expression of Hsp72 in the absence (but not in presence) of tetracycline was confirmed by immunoblotting with anti-Hsp72 antibody.

Figure 13A:
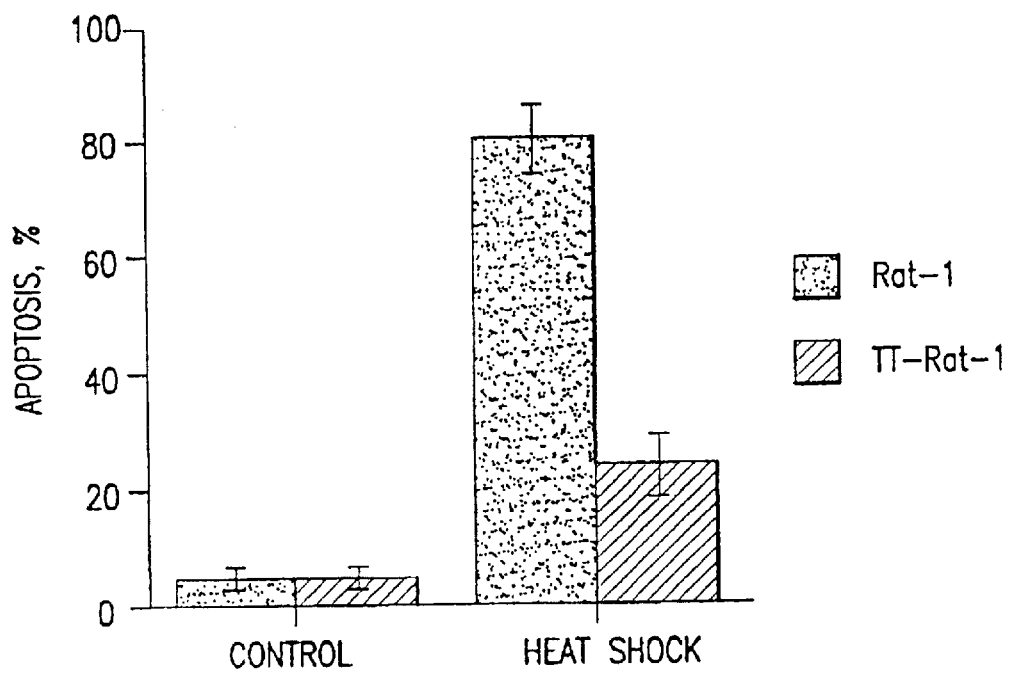
Figure 13B:
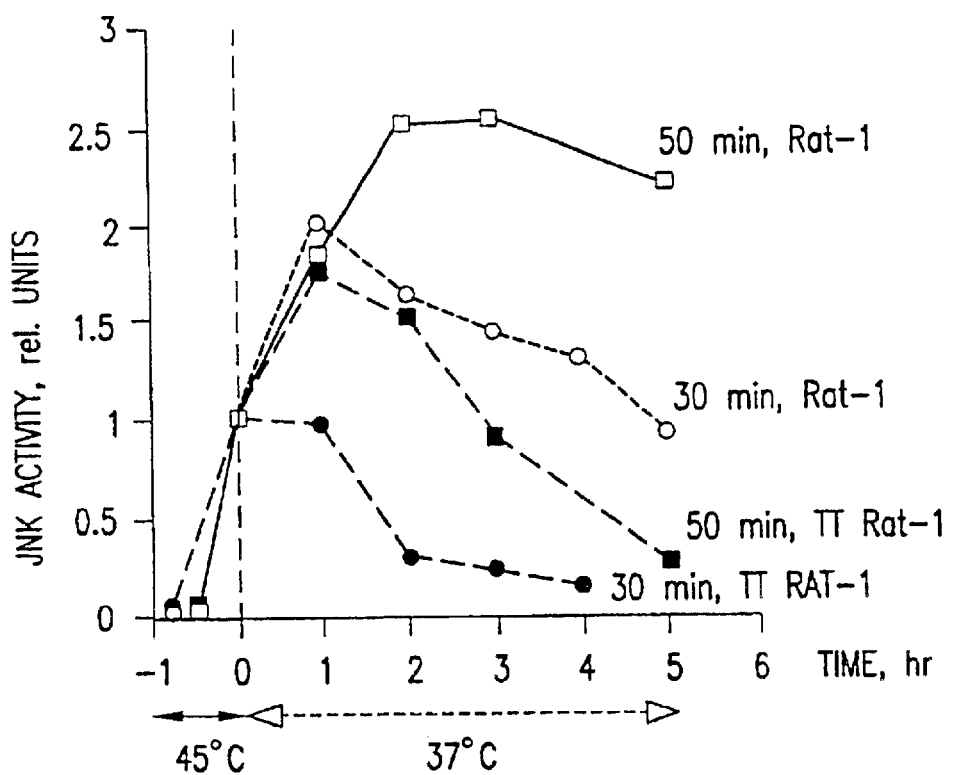

FIGS. 13A–B. Thermotolerance induced by mild heat pretreatment associates with acceleration of JNK inactivation. Rat-1 cells were pretreated with mild heat shock (45° C., 15 min) with subsequent recovery for 16 h at 37° C. Such treatment leads to marked accumulation of Hsp72 (not shown). These cells (TT Rat-1) and untreated cells were subjected to a severe heat shock (45° C., 30 or 50 min) and their apoptosis (A) and JNK activity (B) was measured as described earlier. (FIG. 13A) Apoptosis in control and thermotolerant cells 24 h after heat shock (45° C., 50 min.). (FIG. 13B) JNK1 activity in control and thermotolerant cells after heat shock at 45° C. for 30 or 50 min.

Figure 14A:
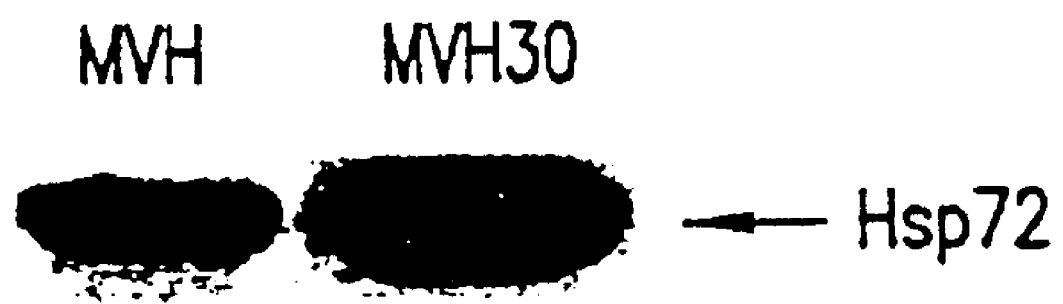
Figure 14B:
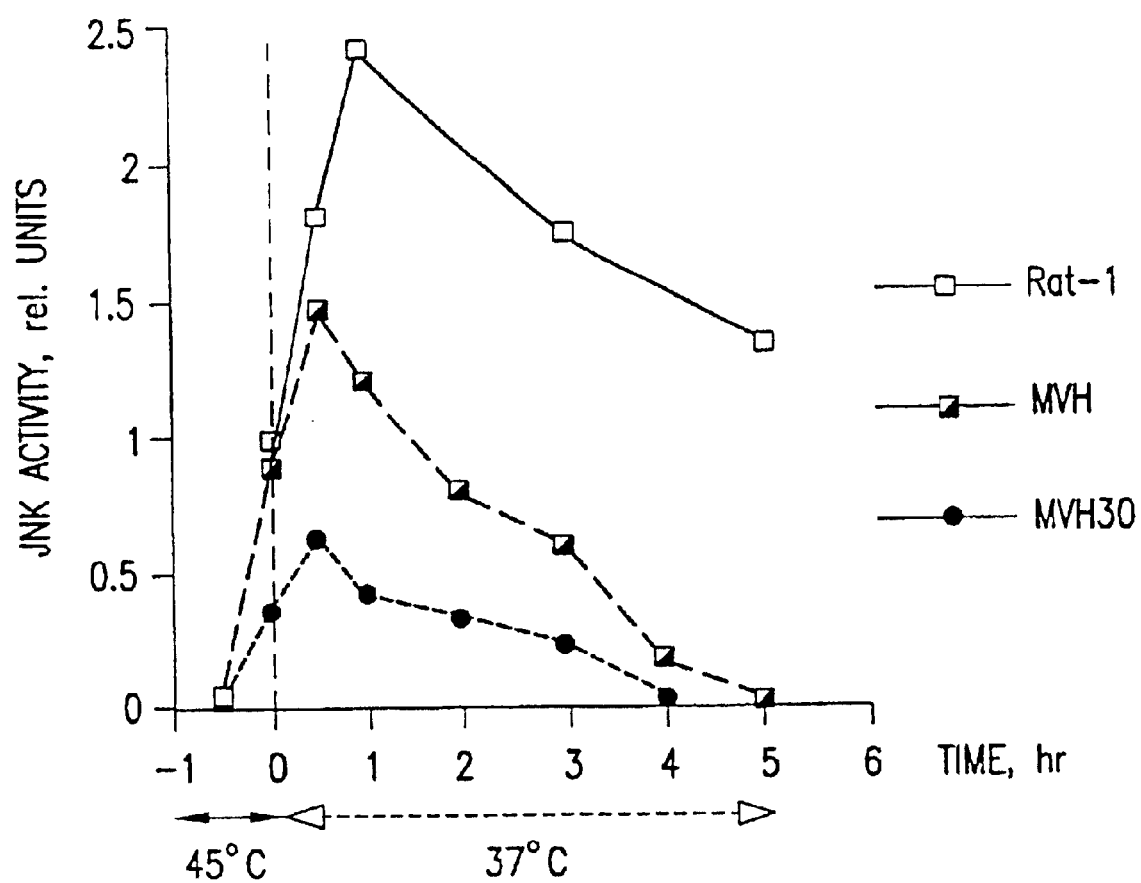
Figure 14C:
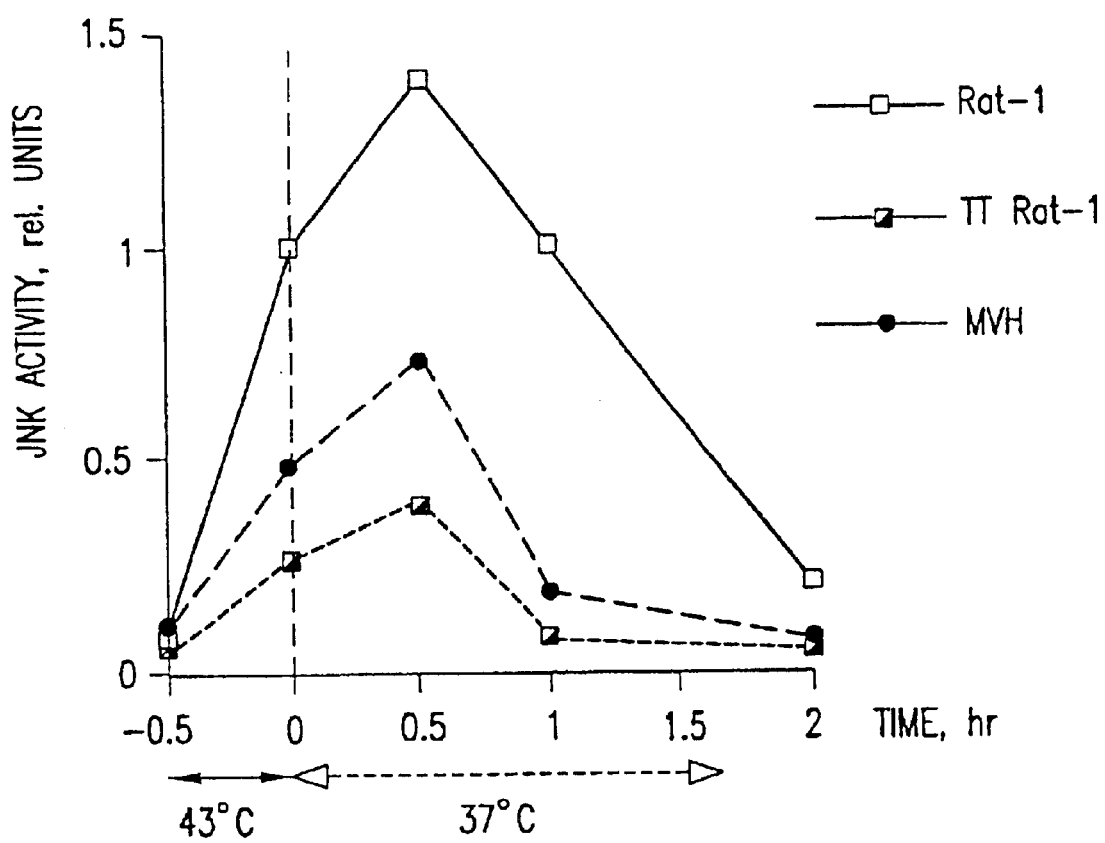

FIGS. 14A–C. Suppression of heat-induced JNK activation by Hsp72 depends on its expression level and on the severity of heat shock. (FIG. 14A) MVH30 clone has increased level of Hsp72. (FIG. 14B) Initial JNK activation after severe heat shock (45° C., 30 min) is suppressed in MVH30 cells. (FIG. 14 C) Expression of Hsp72 in MVH cells suppresses initial JNK activation after mild heat shock (43° C., 30 min). Control (Rat-1), Hsp72-expressing variants (MVH and MVH30), and thermotolerant (TT) were subjected to heat shock and their JNK1 activity was measured by immunoblot at the time points indicated. The cells acquired thermotolerance after pretreatment with mild heat shock (45° C., 15 min) followed by subsequent recovery for 16 hr at 37° C.

FIGS. 15A–E. Expression of ATPase-deficient mutant of Hsp72 (CTF) in Rat-1 cells accelerates JNK inactivation and protects against apoptosis. Rat-1 cells and their variant expressing C-terminal fragment (CTF) of Hsp72 were subjected to heat shock (45° C., 30 or 50 min) and then the rate of JNK inactivation, the activity of JNK phosphatase, and apoptosis were determined. (FIG. 15A) CTF expression in Rat-1 cell variant (as measured by immunoblot with SPA820 Mab to Hsp72/Hsc73). (FIG. 15B) CTF expression accelerate JNK inactivation after heat shock. Control and CTF-expressing cells were treated at 45° C. for 30 or 50 min and JNK1 activity was measured by immunoblot at the time points indicated. (FIG. 15C) CTF expression increases JNK phosphatase activity after heat shock. Cells were subjected to heat shock (45° C., 30 min) following by 2 hr of recovery at 37° C. and JNK1 dephosphorylation (JNTK phosphatase activity) was measured under the chase conditions. (FIG. 15D) CTF expression protect cells against heat-induced apoptosis. Cells were subjected to heat shock (45° C., 50 min) and the apoptosis (mean+/−SD) was determined 24 h later.

FIG. 16A. Nucleotide sequence of the Hsp72 gene (SEQ ID NO: 1).

FIG. 16B. Deduced amino acid sequence of th eHsp 72 Protein (SEQ ID NO:2).

5. DETAILED DESCRIPTION OF THE INVENTION

The invention described in the subsections below encompasses screening methods (also referred to as assays) for the identification of compounds which can be used to regulate the expression and/or activity of Hsp72. The invention also encompasses antagonists of Hsp72 including small molecules, large molecules, and antibodies, as well as nucleotide sequences that can be used to inhibit Hsp72 gene expression (e.g. antisense and ribozyme molecules). In particular, cellular and non-cellular based assays are described that can be used to identify compounds that interact with the Hsp72 gene product, e.g., modulate the activity of Hsp72 and/or bind to the Hsp72 gene product. The invention also encompasses the use of such assays to screen for compounds that modulate Hsp72 gene expression.

The invention further provides compositions and methods for treating proliferative disorders mediated by the elevated expression of the Hsp72 gene product. The present invention provides methods for selecting an effective compound to administer to a subject having a Hsp72 mediated proliferative disorder. Such methods are based on the discovery that overexpression of Hsp72 results in oncogenic transformation of cells. Moreover, suppression of Hsp72 expression in such cells results in reversion of the cells to a non-transformed phenotype. In addition, screening methods of the invention are based on the discovery that expression of the C-terminal protein binding domain of Hsp72 is sufficient to confer the transformed phenotype.

5.1. The Role of Hsp72 in the Regulation of Cell Proliferation

The specific role of Hsp72 in cellular transformation was investigated by forcing the constitutive expression of Hsp72, or inducing increased levels of Hsp72 expression in mammalian cells. The results indicate that Hsp72 plays an active role in the process of cellular transformation.

In order to assess the role of Hsp72 in cellular transformation, Rat-1 fibroblasts were stably transfected with Hsp72. Upon expression of Hsp72 the cells cost contact inhibition and formed foci characteristic for oncogenic transformed cells. Furthermore, the cells were able to grow in an anchorage-independent manner and formed colonies in soft agar. When the stubly transfected cells were injected subcutaneously into nude mice, the mice developed tumors.

In addition, the forced expression of Hsp72 in Rat-1 cells was obtained using an adenovirus based expression system under the control of a tetracycline-inhibitable transactivator. Normal contact inhibition was observed when infected cells were maintained in the presence of tetracycline. However, in the absence of tetracycline, which induces the expression of Hsp72, the cells lost contact inhibition and formed foci after reaching confluency. Inducible expression of Hsp72 also resulted in loss of anchorage dependency and to the formation of colonies in soft agar. Furthermore, upon addition of tetracycline and a return of Hsp72 to its normal level, contact inhibition was restored and the cells lost their potential to form colonies in soft agar.

Hsp72 contains two active domains—a C-terminal peptide binding domain (C-terminal fragment, CTF) which is capable of binding unfolded peptides, and an ATPase domain which is necessary for the release of bound polypeptides. In order to assess whether the CTF region was sufficient to transform cells, cells were stably transfected with a nucleic acid molecule encoding the CTF region of Hsp72. Cells transfected with this nucleic acid molecule exhibited loss of contact inhibition as exemplified by the formation of foci upon reaching confluency, as well as exhibiting anchorage-independent growth. Moreover, when injected into nude mice, CTF-expressing cells caused tumor formation which appeared to occur at a faster ate and more aggressively than when full length Hsp72-expressing cells were used. The observed results indicate that the transforming ability of Hsp72 is conferred by its peptide binding domain and does not require an ATP ase activity.

It was previously demonstrated that the anti-apoptotic effect of transiently expressed Hsp72 is due to suppression of activity of the stress kinase JNK, an early component of the apoptotic pathway initiated by heat shock. Experiments were conducted to determine the role of Hsp72 in heat-induced apoptosis. In particular, the effects of constitutively expressed Hsp72 on activation of JNK and apoptosis in Rat-1 cells was examined. The data indicated that the level of heat-induced apoptosis directly correlated with the duration of JNK activity following heat shock rather that with initial JNK activation. Constitutively expressed Hsp72 strongly reduced the duration of JNK activity, while it did not suppress initial JNK activation. These effects were due to Hsp72-mediated acceleration of JNK dephosphorlation. Inhibition of the effect of Hsp72 on duration of JNK activity by the addition of vanadate, an inhibitor of JNK phosphatase, completely reversed anti-apoptotic effect of Hsp72. Therefore, suppression of heat-induced apoptosis by Hsp72 is exerted through its effects on JNK activation. In addition, it was demonstrated that the C-terminal fragment of Hsp72, which lacks ATPase activity, accelerated JNK dephosphorylation, reduced the duration of JNK activity and suppressed heat-induced apoptosis. Thus, protein refolding activity is dispensable for the effects of Hsp72 on JNK and on apoptosis.

5.2. Expression of the Hsp272 Protein

Hsp72 gene sequences, Hsp72 proteins, including peptide fragments and truncated or deleted forms of Hsp72 can be prepared for use as reagents in screening assays designed to identify compounds capable of regulating Hsp72 expression and/or activity. In an embodiment of the invention, the C-terminal protein binding domain of the Hsp72 protein, which is sufficient for transformation of cells, may be expressed and utilized in the screening assays of the invention.

Hsp72 proteins, peptides, and/or fusion proteins can be prepared by various recombinant DNA techniques routinely used by those skilled in the art. For preparation of Hsp72, a nucleic acid molecule encoding Hsp72, or alleles of Hsp72, can be obtained and ligated into various host-expression vector systems. The Hsp72 DNA sequence (SEQ ID NO: 1) is presented in FIG. 16A and the amino acid sequence (SEQ ID NO:2) is presented in FIG. 16B. In addition sequences encoding truncated Hsp72 may also be prepared using recombinant DNA techniques. The amino acids which delineate the functional domains, such as the ATPase domain and the C-terminal protein binding domain are well known to those skilled in the art and may be expressed recombinantly as well.

An Hsp72 encoding nucleic acid molecule may be obtained using a polymerase chain reaction (PCR) and oligonucleotide primers representing known Hsp72 sequences for amplification of Hsp72 sequences. The synthetic oligonucleotides may be utilized as primers to amplify by PCR Hsp72 sequences from a source (RNA or DNA), preferably a cDNA library. PCR can be carried out, e.g., by use of a Perkin-Elmer Cetus thermal cycler and Taq polymerase (GENE Amp"). Alternatively, a nucleic acid molecule encoding Hsp72 may be obtained by standard procedures known in the art such as cDNA cloning, or by cloning of genomic DNA, or fragments thereof (See, for example, Sambrook et al., 1989, Molecular Cloning, A Laboratory Manual, 2d Ed., Cold Spring Harbor Laboratory Press, Cold Spring Harbor, N.Y. Glover, D. M. (ed.), 1985, DNA Cloning: A Practical Approach MRL Press, Ltd., Oxford, U.K. Vol. I, II.).

The nucleotide sequence coding for a Hsp72 protein or a functionally active analog or fragment or other derivative thereof can be inserted into an appropriate expression vector, i.e., a vector which contains the necessary elements for the transcription and translation of the inserted protein-coding sequence. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast (e.g. Pichia, Hanensula) containing yeast vectors, or bacteria transformed with bacteriophage, DNA, plasmic DNA, or cosmid DNA. The expression elements of vectors vary in their strengths and specificities. Depending on the host-vector system utilized, any one of a number of suitable transcription and translation elements may be used. In specific embodiments, the Hsp72 gene is expressed, or a sequence encoding a functionally active portion of the Hsp72 gene such as the C-terminal fragment is expressed. Expression from certain promoters can be elevated in the presence of certain inducers; thus, expression of the genetically engineered Hsp72 protein may be controlled.

In addition, fusion proteins in which the full length Hsp72, or truncated Hsp72 protein is fused to an unrelated protein may be produced for use as reagents in the screening assays of the invention. A number of expression vectors may be advantageously selected for expression of fusion proteins, such as pGEX vectors that express foreign polypeptides as fusion proteins with glutathione S-transferase (GST). In general, such fusion proteins are soluble and can be easily purified from lysed cells by adsorption to glutathione-agarose beads. Alternatively, vectors may be used that express fusion proteins containing an amino-terminal tag consisting of six histidine residues. Such fusion proteins can be purified by adsorption to an $Ni^{2+}$ nitriloacetic acid-agarose column followed by elution with imidazole-containing buffers.

5.3. Screening Assays for Compounds that Regulate the Proliferation of Cells

A number of different assay systems, described in detail below, can be designed and used to identify compounds that modulate Hsp72 activity or Hsp72 gene expression, and therefore, modulate proliferation of cells.

In accordance with the invention, non-cell based assay systems may be used to identify compounds that interact with, e.g., bind to Hsp72. Such compounds may act as antagonists of Hsp72 activity and may be useful in treatment of proliferative disorders such as cancer.

To this end, soluble Hsp72 may be recombinantly expressed and utilized in non-cell based assays to identify compounds that bind to Hsp72. Full length Hsp72, fusion Hsp72 proteins, or peptides corresponding to one or more functional domains such as the C-terminal peptide binding domain, may be used in non-cell based assay systems to identify compounds that bind to Hsp72.

The principle of the assays used to identify compounds that bind to Hsp72 involves preparing a reaction mixture of the Hsp72 gene product and the test compound under conditions and for a time sufficient to allow the two components to interact and bind, thus forming a complex that can be removed and/or detected in the reaction mixture. These assays may be conducted in a variety of different ways. For example, one method to conduct such an assay involves anchoring a Hsp72 gene product or a test compound onto a solid support and detecting Hsp72 gene product/test compound complexes formed on the solid support at the end of the reaction. In one embodiment of such a method, the Hsp72 protein, fusion protein, or peptide corresponding to a functional domain such as the C-terminal peptide binding domain, may be anchored onto a solid support, and the test compound, which is not anchored, may be labeled, either directly or indirectly.

In practice, microtitre plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody specific for Hsp72 may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid support can be accomplished in a number of ways. Where the previously non-immobilized component is pre-labeled, the detection of label immobilized on the surface indicates that complexes were formed.

Alternatively, a reaction may be conducted in a liquid phase, the reaction products separated from unreacted components, and complexes detected; e.g., using an immobilized antibody specific for the Hsp72 protein or the test compound to anchor any complexes formed in solution.

In addition to non-cell based assay systems, cell based assay systems may be used to screen for compounds that modulate the activity of the Hsp72 protein and thereby, modulate Hsp72 mediated cellular transformation. To this end, host cells genetically engineered to express constitutive levels of Hsp72, or host cells that overexpress Hsp72, may be used for screening purposes. Preferably, the host cells to be used to screen for compounds are cells that respond to overexpression of Hsp72 as measured by a chemical, physiological, biological or phenotypic change, e.g., induction of a host cell gene or a reporter gene, change in host cell kinase or phosphatase activity, proliferation, etc.

In utilizing such cell systems, the cells expressing the Hsp72 are exposed to a test compound or to a vehicle control. After exposure, the cells are assayed to measure the biological activity of the Hsp72 protein. For example, constitutive expression or overexpression of Hsp72 is associated with cellular transformation; thus, in a specific embodiment of the invention assays may be designed to increase Hsp72 induced cellular transformation. The ability of a compound to decrease the level of transformation above those levels seen with cells treated with a vehicle control indicates that the test compound inhibits signal transduction mediated by the Hsp72 protein.

In a specific embodiment of the invention, after exposure of cells to a test compound, cells may be assayed for their ability to grow in an anchorage-independent manner and form colonies in soft agar. Alternatively, the cells can be assayed for contact inhibition or for their ability to form tumors in nude mice.

Additionally, following exposure to the test compound, the cells may be assayed to measure the activity of components of the Hsp72 signal transduction pathway. For example, as described herein, the Hsp72 protein is capable of preventing heat induced apoptosis. Thus, in utilizing the cell based assay systems of the invention, cells expressing Hsp72 can be exposed to a test compound or to a vehicle control. After exposure, the cells can be assayed for heat induced apoptosis using any of the variety of different methods available for measuring apoptosis. Such assays designed to measure apoptosis include the terminal deoxynucleotidly transferase mediated dUTP nick end labeling (TUNEL) assay (Kebers et al., 1998, Experimental Cell Research 240:197–205); assays to detect activated caspases (Janicke et al., 1998, J. Biol. Chem. 273:9357–9360); DNA ladder gel assays to detect fragmented DNA by gel electrophoresis (Bursch et al., 1996, Carcinogenesis 17:1595–1607); assays to detect bcl-2 and bax protein levels (Wuerzberger et al., 1998, Cancer Research 58:1876–1885); Hoechst/DAPI staining to detect nuclear condensation in apoptotic cells (Bursch et al., 1998, Carcinogenesis 17:1595–1607); Annexin V staining of phospatidyl serine on the cytoplasmic membrane (van Engeland et al., 1996, Cytometry 24:131–139); analysis of DNA content by propidium iodide staining followed by flow cytometry (Sherwood et al., Methods in Cell Biology 46:77–97, and morphological studies using electron and phase contrast microscopy (Bursch et al., Carcinogenesis 17:1595–1607). The ability of a test compound to increase the levels of apoptosis, above those levels seen with cells treated with a vehicle control, indicates that the test compound inhibits signal transduction mediated by Hsp72.

In addition, screening assays may be performed to identify compounds capable of mediating Hsp72 activation of the JNK phosphatase. In utilizing such an assay system, cells expressing Hsp72 are exposed to a test compound or to a vehicle control. After exposure, the cells are exposed to heat induced stress, followed by an assay to measure the level of active JNK phosphatase. The ability of a test compound to decrease the levels of JNK phosphatase, above those levels seen with cells treated with a vehicle control, indicates that the test compound inhibits signal transduction mediated by Hsp72 activation of the JNK phosphatase.

The level of JNK phosphatase activation can be measured using a variety of different methods. For example, in vivo JNK phosphatase activity may be measured by assaying for levels of phosphorylated JNK as described in Meriin et al. (1999, Mol. Cel. Biol.). The rate of JNK dephosphorylation can be assessed by immunoblotting with an antibody which specifically recognizes the activated (phosphorylated) form of JNK.

By way of example, diversity libraries, such as random or combinational peptide or nonpeptide libraries can be screened for molecules that specifically bind to Hsp72. Many libraries are known in the art that can be used, e.g., chemically synthesized libraries and recombinant libraries such as phage display libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Hsp72 128:59–65; and PCT Publication No. WO 94/18318 dated Aug. 18, 1994.

By way of examples, peptide libraries (Simon et al., 1992, Proc. Natl. Acad. Sci. USA 89:9367–9371) can also be used, as well as libraries in which the amide functionalities in peptides have been permethylated to generate a chemically transformed combinatorial library, as described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

Hsp72 gene product can interact in vivo with one or more cellular macromolecules, such as nucleic acid molecules or proteins. In yet another embodiment of the invention, the two hybrid system for selecting interacting proteins in yeast (Fields and Song, 1989, Nature 340:245–246; Chin et al., 1991, Proc. Natl. Acad. Sci. USA 88:9578–9582) can be used to identify molecules that specifically bind to Hsp72 or derivatives thereof. Once such interacting proteins are identified, they may be used to identify compounds that stabilize or disrupt such interactions, which can be useful in regulating the activity of the Hsp72 protein.

To assay for compounds that interfere with the interaction of Hsp72 protein with cellular macromolecules, either the Hsp72 protein or the macromolecule may be anchored onto a solid phase. Complex formation can be detected at the end of the reaction comparing complex formation in the presence or absence of test compound. The order of addition of test compounds can be varied to obtain different information about the compounds being tested. For example, test compounds that interfere with the interaction by competition can be identified by conducting the reaction in the presence of the test compound, i.e., by adding the test compounds to the reaction mixture prior to or simultaneously with the Hsp72 protein and the cellular binding partner. Alternatively, test compounds that disrupt preformed complexes, i.e, those compounds with higher binding constants that displace one of the components from the complex, can be tested by adding the test compound to the reaction after the complexes have formed.

Assays may also be designed to screen for compounds that regulate Hsp72 gene expression at the transcriptional level. In one embodiment, DNA encoding a reporter molecule can be linked to a regulatory element of the Hsp72 gene and used in appropriate intact cells, cell extracts or lysates to identify compounds that modulate Hsp72 gene expression. Reporter molecules that may be used in the practice of the invention include but are not limited to chloramphenicol acetyltransferase (CAT), luciferase, beta glucuronidase (GUS), growth hormone, or placental alkaline phosphatase (SEAP). Appropriate cells or cell extracts are prepared from any cell type that normally expresses the Hsp72 gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound. Compounds that decrease the level of Hsp72 gene expression at the transcriptional level may be useful for treatment of proliferative disorders.

The assays described above can identify compounds which affect Hsp72 activity. Compounds that may affect Hsp2 activity include but are not limited to compounds that bind to the Hsp72 functional domains and block activation (antagonists). Compounds that affect Hsp72 activity by affecting Hsp72 gene expression, including molecules that affect transcription or interfere with splicing events so that expression of the full length or the truncated form of the Hsp72 can be modulated can also be identified using the screens of the invention. However, it should be noted that the assays described can also identify compounds that modulate Hsp72 signal transduction (e.g., compounds which affect downstream signaling events and participate in transducing the signal activated by Hsp72). The identification and use of such compounds which affect signaling events downstream of Hsp72 and thus modulate effects of Hsp72 on the development of proliferative disorders are within the scope of the invention.

The present invention also provides screening methods for the identification of, compounds that either directly, or indirectly, regulate JNK phosphatase activity. The screening methods are based on the discovery that Hsp72 exerts its anti-apoptopic effect through acceleration of JNK dephosphorylation. In utilizing such an assay system, cells may be exposed to a test compound or to a vehicle control. After exposure to the test compound, the cells are exposed to heat induced stress, followed by an assay to measure the level of JNK phosphatase activation. The ability of a test compound to decrease the levels of JNK phosphatase, above those levels seen with cells treated with a vehicle control, indicates that the test compound inhibits JNK phosphatase. The level of JNK phosphatase activation can be measured using a variety of different methods. For example, in vivo JNK phosphatase activity may be measured by assaying for levels of phosphorylated JNK as described in Meriin et al. (1999, Mol. Cel. Biol.). The rate of JNK dephosphorylation can be assessed by immunoblotting with an antibody which specifically recognizes the activated (phosphorylated) form of JNK. Alternatively, the assays may be designed to include labeled ATP, such as radioactively labeled $^{32}$P-ATP which provides a means for detecting the level of phosphorylation of the JNK kinase in the presence and absence of the test compound. In yet another embodiment of the invention the amount of activated JNK kinase activity in cell lysates prepared from cells exposed to a test compound can be compared to lysates prepared from cells exposed to a vehicle control using a JNK kinase substrate. An increase in detectable JNK kinase activity following exposure of the cell heat induced stress in the presence of a test compound and indicates that the test compound inhibits the activity of the JNK phosphatase.

Once a compound capable regulating the activity and/or expression of Hsp72 has been identified, the compound is tested for its ability to inhibit cellular transformation in cells constitutively expressing Hsp72 or over expressing Hsp72. Such assays include the ability of the compound to inhibit anchorage-independent growth and form colonies in soft agar and/or restore contact inhibition to the cells. The compounds of the invention are preferably tested in vitro, and then in vivo for the desired therapeutic activity, prior to use in humans. For example, in vitro assays, including in vitro cell culture assays in which a patient tissue sample is grown in culture can be used to determine whether administration of an identified compound.

5.4. Antisense Regulation of Hsp72 Expression

In a specific embodiment, Hsp72 function is inhibited by use of Hsp72 antisense nucleic acids. The present invention provides the use of nucleic acids that are antisense to a Hsp72 or cDNA encoding Hsp72 or a portion thereof (see, FIG. 16A). A Hsp72 "antisense" nucleic acid as used herein refers to a nucleic acid capable of hybridizing to a portion of a Hsp72 RNA by virtue of some sequence complementarity. The antisense nucleic acid may be complementary to a coding and/or noncoding region of a Hsp72 mRNA. Such antisense nucleic acids have utility as inhibitors of Hsp72 function, and can be used in the treatment or prevention of Hsp72 mediated proliferative disorders.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

The invention further provides pharmaceutical compositions comprising an effective amount of the Hsp72 antisense nucleic acids of the invention in a pharmaceutically acceptable carrier.

The Hsp72 antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, and can be single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci.

84:648–652; PCT Publication No. WO 88/09810, published Dec. 15, 1988), hybridization-triggered cleavage agents (see, e.g., Krol et al.1 1988, BioTechniques 6:958–976) or intercalating agents (see, e.g., Zon, 1988, Pharm. Res. 5:539–549).

In a preferred aspect of the invention, a Hsp72 antisense oligonucleotide is provided, preferably of single stranded DNA. In a most preferred aspect, such an oligonucleotide comprises a sequence antisense to the sequence encoding the C-terminal fragment of the Hsp72 protein. The oligonucleotide may be modified at any position on its structure with substituents generally known in the art.

The Hsp72 antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 51-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an a-anomeric oligonucleotide. An a-anomeric oligonucleotide forms specific double-stranded hybrids with complementary RNA in which, contrary to the usual O-units, the strands run parallel to each other (Gautier et al., 1987, Nucl. Acids Res. 15:6625–6641).

The oligonucleotide may be conjugated to another molecule, e.g., a peptide, hybridization triggered cross linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:74487451), etc.

In a specific embodiment, the Hsp72 antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 21-0-methylribonucleotide (Inoue et al., 1987, Nucl. Acids Res. 15:6131–6148), or a chimeric RNA–DNA analogue (Inoue et al., 1987, FEBS Lett. 215:327–330).

In an alternative embodiment, the Hsp72 antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Hsp72 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmic, viral, or others known in the art, used for replication and expression in mammalian cells. Expression of the sequence encoding the Hsp72 antisense RNA can be by any promoter know in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 31 long terminal repeat of Rous sarcoma virus (Yamamoto et al., 1980, Cell 22:787797), the herpes thymidine kinase promoter (Wagner et al., 1981, Proc. Natl. Acad. Sci. U.S.A. 78:1441–1445), the regulatory sequences of the metallothionein Hsp72 (Brinster et al., 1982, Nature 296:39–42), etc.

The antisense nucleic acids of the invention comprise a sequence complementary to at least a portion of an RNA transcript of a Hsp72, preferably a human Hsp72. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Hsp72 antisense nucleic acids, a single strand of the duplex DNA may thus be tested, or triplex formation may be assayed. The ability to hybridize will depend on both the degree of complementarity and the length of the antisense nucleic acid. Hsp72 rally, the longer the hybridizing nucleic acid, the more base mismatches with a Hsp72 RNA it may contain and still form a stable duplex (or triplex, as the case may be). One skilled in the art can ascertain a tolerable degree of mismatch by use of standard procedures to determine the melting point of the hybridized complex.

The Hsp72 antisense nucleic acids can be used to inhibit cell proliferation in transformed cell types that overexpresses Hsp72. The an Hsp72 antisense nucleic acids may be used to treat proliferative disorders such as cancers disorders.

Cell types which express or overexpress Hsp72 RNA can be identified by various methods known in the art. Such methods include but are not limited to hybridization with a Hsp72-specific nucleic acid (e.g. by Northern hybridization, dot blot hybridization, in situ hybridization), observing the ability of RNA from the cell type to be translated in vitro into Hsp72, immunoassay, etc. In a preferred aspect, primary tissue from a subject can be assayed for Hsp72 expression prior to treatment, e.g., by immunocytochemistry or in situ hybridization.

Pharmaceutical compositions of the invention comprising an effective amount of a Hsp72 antisense nucleic acid in a pharmaceutically acceptable carrier, can be administered to a subject having a disease or disorder which is of a type that expresses or overexpresses Hsp72 RNA or protein.

The amount of Hsp72 antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Hsp72 antisense nucleic acids are administered via liposomes, microparticles, or microcapsules. In various embodiments of the invention, it may be useful to use such compositions to achieve sustained release of the Hsp72 antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.5. Generation of Antibodies to Hsp72 Proteins and Derivatives Thereof

According to the invention, Hsp72 protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to Hsp72 protein are produced. In another embodiment, antibodies to a domain of a Hsp72 protein are produced. In a specific embodiment, fragments of a Hsp72 protein identified as hydrophilic are used as immunogens for antibody production.

Various procedures known in the art may be used for the production of polyclonal antibodies to a Hsp72 protein or derivative or analog. In a particular embodiment, rabbit polyclonal antibodies to an epitope of a Hsp72 protein can be obtained. For the production of antibody, various host animals can be immunized by injection with the native Hsp72 protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Hsp72 protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBVhybridoma technique to produce human monoclonal antibodies (Cole et al., 1985, in Monoclonal Antibodies and Cancer Therapy, Alan R. Liss, Inc., pp. 77–96). An additional embodiment of the invention utilizes the techniques described for the construction of Fab expression libraries (Huse et al., 1989, Science 246:12751281) to allow rapid and easy identification of monoclonal Fab fragments with the desired specificity for Hsp72 protein derivatives, or analogs.

In the production of antibodies, screening for the desired antibody can be accomplished by techniques known in the art, e.g. ELISA (enzyme-linked immunosorbent assay). For example, to select antibodies which recognize a specific domain of a Hsp72 protein, one may assay generated hybridomas for a product which binds to a Hsp72 fragment containing such domain.

5.6. Compositions and Uses

The present invention provides for treatment or prevention of various diseases and disorders by administration of a compound that regulates the activity of the Hsp72 protein. Such compounds include anti-Hsp72 antibodies, Hsp72 antisense nucleic acids, and compounds identified as Hsp72 antagonists. Disorders involving aberrant cell proliferation are treated by administration of a compound that inhibits Hsp72 function. Disorders of cell proliferation, such as cancers, are treated or prevented by administration of a compound that antagonizes, or inhibits, Hsp72 function. Diseases and disorders involving cell proliferation that can be treated or prevented include cancers such as leukemia, lymphoma, solid tumors such as sarcomas and carcinomas, breast cancer, prostate cancer.

The compounds of the invention that inhibit Hsp72 activity can also be administered to treat premalignant conditions and to prevent progression to a neoplastic or malignant state. Such prophylactic or therapeutic use is indicated in conditions known or suspected of preceding progression to neoplasia or cancer, in particular, where nonneoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68–79.)

Alternatively or in addition to the presence of abnormal cell growth characterized as hyperplasia, metaplasia, or dysplasia, the presence of one or more characteristics of a transformed phenotype, or of a malignant, phenotype, displayed in vivo or displayed in vitro by a cell sample from a patient, can indicate the desirability of prophylactic/therapeutic administration of a compound that promotes Hsp72 function. Such characteristics of a transformed phenotype include morphology changes, decreased substratum attachment, loss of contact inhibition, loss of anchorage dependence and decreased serum requirement.

In specific embodiments, compounds that inhibit Hsp72 function are administered to a subject having a disease or disorders mediated by an increase, relative to normal levels, of Hsp72 protein or activity. The increased level in Hsp72 protein or function can be readily detected, e.g., by obtaining a patient tissue sample (e.g., from biopsy tissue) and assaying for RNA or protein levels, structure and/or activity of the expressed Hsp72 RNA or protein. Many methods standard in the art can be thus employed, including but not limited to kinase assays, immunoassays to detect and/or visualize Hsp72 protein (e.g., Western blot, immunoprecipitation followed by sodium dodecyl sulfate polyacrylamide gel electrophoresis, immunocytochemistry, etc.) and/or hybridization assays to detect Hsp72 expression by detecting and/or visualizing Hsp72 mRNA (e.g., Northern assays, dot blots, in situ hybridization, etc.), etc.

Diseases and disorders involving cell proliferation are treated or prevented by administration of a compound that antagonizes (inhibits) Hsp72 function. Compounds that can be used include but are not limited to anti-Hsp72 antibodies (and fragments and derivatives thereof containing the binding region thereof) and Hsp72 antisense nucleic acids. Other compounds that inhibit Hsp72 function can be identified by use of the cell based and non-cell based assays described herein, e.g., based on their ability to inhibit Hsp72 function. Preferably, suitable in vitro or in vivo assays, are utilized to determine the effect of a specific compound and whether its administration is indicated for treatment of the proliferative disorder.

Compounds for use in treatment of Hsp72 mediated proliferative disorders can be tested in suitable animal model systems prior to testing in humans, including but not limited to rats, mice, chicken, cows, monkeys, rabbits, etc. For in vivo testing, prior to administration to humans, any animal model system known in the art may be used.

The invention provides methods of treatment of proliferative disorders by administration to a subject of an effective amount of a compound that inhibits Hsp72 mediated transformation. In a preferred aspect, the subject is an animal, and is preferably a mammal, and most preferably human.

Various delivery systems are known and can be used to administer a compound that is capable of inhibiting the expression and/or activity of the Hsp72 protein, e.g. encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid, such as an antisense nucleic acid, as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or preneoplastic tissue.

In another embodiment, the compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas; J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the compound target, i.e., the tumor, thus requiring only a fraction of the systemic dose (see, e.g., Goodson, in Medical Applications of Controlled Release, supra, Vol. 2, PP. 115–138 (1984)). Other controlled release systems are discussed in the review by Langer (Science 249:1527–1533 (1990)).

The present invention also provides pharmaceutical compositions. Such compositions comprise a therapeutically effective amount of the compound capable of regulating the expression and/or activity of the Hsp72 protein, and a pharmaceutically acceptable carrier. In a specific embodiment, the term "pharmaceutically acceptable" means approved by a regulatory agency of the Federal or a state government or listed in the U.S. Pharmacopoeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the compound, preferably in purified form, together with a suitable amount of carrier so as to provide the form for proper administration to the patient. The formulation should suit the mode of administration.

The amount of the compound of the invention which will be effective in the treatment of a particular proliferative disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The invention also provides a pharmaceutical pack or kit comprising one or more containers filled with one or more of the ingredients of the pharmaceutical compositions of the invention. optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE
Regulation of Cell Proliferation by the Hsp72 Protein

The subsection below describes experimental data demonstrating that Hsp72 plays an active role in the process of oncogenic transformation. When Hsp72 was expressed in Rat-1 fibroblasts either constitutively or from an adenovirus-based construct, cells became oncogenically transformed by the following criteria: loss of contact inhibition and formation of foci characteristic for oncogenically transformed cells; acquisition of the ability to grow in an anchorage-independent manner and to form colonies in soft agar; generation of tumors upon injection into mice. Furthermore, inhibition of the Hsp72 expression led to the reversal of the transformed phenotype. Experiments were also conducted demonstrating that the oncogenic potential of Hsp72 is confined to the C-terminal peptide binding domain since the expression of this domain alone was sufficient for oncogenic transformation of Rat-1 cells.

6.1. Materials and Methods 6.1.1. Cells

MV6, MVH, and MVHΔBg cells (kindly provided by Dr. Li, Sloan Katering Cancer Institute) are Rat1-derived cell lines obtained by stable transfection with vector alone (MV6), with vector containing human Hsp72 gene (MVH), or with vector expressing the C-terminal fragment of Hsp72 (MVHΔBg) (Li et al., 1992, Proc. Natl. Acad. Sci. USA 89 2036–2040). MV6, MVH and MVHΔBg cells Rat-1 cells were maintained in DME medium supplemented with 10% fetal bovine serum and 200 μg/ml gentamycin, while the parental Rat-1 cells were maintained in the same medium but without gentamycin. Plating of cells in soft agar was carried out as described in Clark et al., 1995.

6.1.2. Adenovirus-based Expression of Hsp72

Recombinant adenovirus vector expressing Hsp72 (ADTR5Hsp72-GFP, curtesy of Dr. Mosser, Biotechnology Research Institute, Montreal) was constructed by cloning a dicistronic transcription unit encoding Hsp72 and Aequorea Victoria green fluorescent protein gene, separated by the encephalomyocarditis virus internal ribosome entry site from pTR-DC/Hsp70-GFP (Mosser et al., 1997a, Mol. Cell Biol, 17: 5317–5327; Mosser et al., 1997b, Biotechniques 22: 150–161) into an adenovirus transfer vector. Expression of this transcription unit is controlled by the tetracycline-regulated transactivator protein tTA (Mosser et al., 1997b, Biotechniques 22: 150–161) which we expressed from a separate recombinant adenovirus. Recombinant adenoviruses were generated by standard techniques as detailed by (Jani et al., 1997, J. Virol. Methods 64: 111–124). Viruses were used at stock concentration of $10^{10}$ pfu/ml. Infection of cells with both viruses simultaneously led to expression of Hsp72 in the absence of tetracycline but not in the presence of 20 nM of anhydrotetracycline. Two-ml cell cultures grown in liquid medium in 35 mm dishes were infected in the presence or the absence of anhydrotetracycline with $3 \cdot 10^7$ pfu of each virus, sufficient for infection of almost 100% cells, and additional $10^7$ pfu of each virus was added on days three and seven. After 24 hours incubation with viruses, cells were washed with PBS and placed in fresh media with or without anhydrotetracycline. For growth in soft agar, cells were infected in liquid medium 24 hours prior to plating in soft agar.

6.1.3. Detection of Hsp72 and CTF

Cells were lysed in a buffer containing 20 mm Tris-HCl, pH 7.4, 50 mm NaCl, 2 mm EDTA, 1% Triton X-100, 25 mm β-glycerophosphate, 10 mm NaF, 1 mm $Na_3VO_4$, and protease inhibitors (1 mm PMSF and 25 μg/ml each of aprotenin, pepstatin, leupeptin), and aliquots were subjected to SDS-PAGE followed by transfer to a nitrocellulose membrane. This membrane was later used for immunoblot with SPA810 antibody specific for Hsp72 or with SPA820 antibody which recognizes CTF (and Hsc73).

6.1.4. In vivo Assay for Tumorogenicity

Cells were collected by centrifugation, washed twice in PBS, and $1 \times 10^5$ or $1 \times 10^6$ cells (specified in figure legends) were injected subcutaneously in 0.1 ml PBS into nude mice which were observed daily.

6.2. Results

Figure 1B:
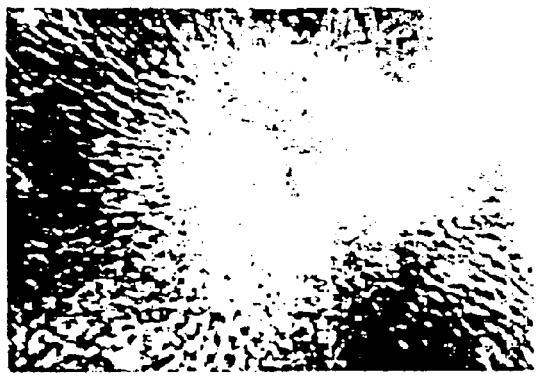
Figure 1C:
Figure 1D:
Figure 5A:
Figure 5B:

Rat-1 fibroblasts are immortalized cells that exhibit strong contact inhibition and, upon reaching the confluent state, form a flat monolayer (FIG. 1A). However, the behavior in the confluent state of cells stably transfected with Hsp72 (Li et al, 1992, Proc. Natl. Acad. Sci. USA 89:2036–2040) was dramatically different. They lost contact inhibition and, within few days after reaching the confluent state, formed foci characteristic for oncogenically transformed cells (FIG. 1B). Moreover, they acquired the ability to grow in an anchorage-independent manner and formed colonies in soft agar which became detectable few days after plating and increased in size for at least three weeks (FIGS. 1C and 5B). Furthermore, when these cells were injected subcutaneously into nude mice, pronounced tumors were formed (FIG. 1D; Table 1).

TABLE 1

Cells constitutively expressing Hsp72 or CTF form tumors in mice

| Cells injected | Number of animals | Number of tumors | Mean time of tumor appearance (days) | Mean weight of tumors at 4 weeks (mg) |
|---|---|---|---|---|
| MV6 | 5 | 0 | — | — |
| MVH | 10 | 10 | 12.6 ± 1.9 | 203 ± 82 |
| MVHΔBg | 10 | 10 | 7.5 ± 0.9 | 699 ± 184 |

Nude mice were injected subcutaneously with $10^6$ of either Rat-1 or MVH or MVHΔBg cells. No tumors were observed with MV6 cells. Each injection with MVH or MVHΔBg cells resulted in a single tumor. After 4 weeks animals were sacrificed, tumors were removed and their weight was determined. Data is shown as means±s.e.m.

Figure 5C:
Figure 5D:
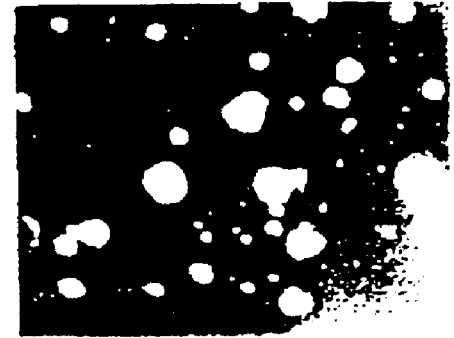

In another approach the expression of Hsp72 in Rat-1 cells was induced using an adenovirus-based expression system under the control of a tetracycline-inhibitable transactivator (Mosser et al, 1997a, Mol. Cell. Biol. 17: 5317–5327). Infection of Rat-1 cells with the recombinant adenovirus resulted in expression of Hsp72 in essentially all cells as judged by proportion of cells expressing GFP in the absence but not in the presence of tetracycline (FIG. 2). Normal contact inhibition was observed when infected cells were maintained in the presence of tetracycline (FIG. 3A). However in the absence of tetracycline they lost contact inhibition and, upon reaching confluency, formed foci within ten days after the initial infection (FIG. 3B). Forced expression of Hsp72 in Rat-1 cells also led to the loss of the anchorage dependency and to the formation of colonies in soft agar whereas no colonies were formed by virus-infected cells in the presence of tetracycline (FIGS. 3C and 5C). To test whether the Hsp72-induced transformed phenotype is reversible, the following experiments were carried out. Rat-1 cells were infected according to our standard protocol (initial infection on day one followed by subsequent addition of virus on days four and seven). On day ten (by this time foci already appeared) cells were replated at low density (approximately 3% of confluency) and reinfected in the presence or in the absence of tetracycline. In the absence of tetracycline high levels of Hsp72 shown in FIG. 2 were sustained and cells formed foci upon reaching a confluent state. By contrast, in the presence of tetracycline Hsp72 dropped to its basal level within three days, and cells formed a flat monolayer. To test for agar colony forming potential, reinfected cells were maintained for three days in liquid medium in the presence or in the absence of tetracycline in order to allow the reduction of Hsp72 levels in cultures containing tetracycline, and then plated in soft agar in the presence or in the absence of tetracycline. Whereas cells formed colonies in the absence of tetracycline, no colonies were observed in the presence of tetracycline. Therefore, upon return of Hsp72 to its normal level, contact inhibition is restored and cells loose the potential to form colonies in soft agar.

Hsp72 contains two active domains—a C-terminal peptide binding domain (C-terminal fragment, CTF) which is capable of binding unfolded polypeptides, and an ATPase domain which is necessary for the release of bound polypeptides. CTF alone was shown to be sufficient for protection of cells from stresses (Li et al, 1992, Proc. Natl. Acad. Sci. USA 89: 2036–2040;). Rat-1 cells stably transfected with CTF (MVHΔBg) exhibited loss of contact inhibition as exemplified by the formation of foci upon reaching confluency (FIG. 4A); they also exhibited an anchorage-independent growth as could be readily seen twelve days after plating in soft agar (FIG. 5). It should be noted that upon longer incubation in agar (for three weeks) it became apparent that colonies formed by MVHΔBg cells were significantly larger than those formed by Rat-1 cell constitutively expressing Hsp72 (FIG. 4B as compared to FIG. 1C; both pictures were taken at the same magnification). No comparison could be made at three weeks with colonies formed by cells expressing Hsp72 from an adenoviral construct since due to the cessation of Hsp72 expression at about two weeks after infection colonies stop growing at this time). Furthermore, when injected into nude mice, CTF-expressing cells caused tumor formation (FIG. 4C) which also appeared to occur even faster and more aggressively than when full length Hsp72-expressing cells were used (Table 1). These results indicate that the transforming ability of Hsp72 is retained by its peptide binding domain and does not require an ATPase activity.

Data described above demonstrate that when elevated levels of Hsp72 are sustained, cells undergo oncogenic transformation. This finding may explain the existence of cellular mechanisms that, despite beneficial properties of Hsp72, preclude stable accumulation of this protein. They may also explain why aged mammalian cells have greatly diminished ability to express Hsp72 in response to stresses (Heydari et al, 1994, Experientia 50 1092–1098). Indeed, aged cells amass substantial levels of abnormal proteins (Rattan, S. 1996, Exp. Gerontol 31 3347), a natural trigger of Hsp72 expression. Consequently, if aged cells were capable of expressing Hsp72, this normally inducible protein would be constitutively produced and thus occur in cells at elevated levels potentially increasing the cancer incidence.

It should be noted that the results described above were obtained using an immortalized cell line. Such a cell has already undergone events on the path towards full transformation. The transforming ability of Hsp72 may not be observed in normal cells with a limited life span which would suggest that in this respect it is a rather typical oncogene. In fact, when Hsp72 was expressed from adenoviral construct in primary human fibroblasts IMR90, no change in phenotype was observed.

7. EXAMPLE

Hsp72 Protects Cells from Heat Induced Apoptosis

The subsection below presents data indicating that the major heat shock protein Hsp72 prevents heat-induced apoptosis. Specifically, the effects of constitutively expressed Hsp72 on activation of JNK and apoptosis in Rat-1 fibroblasts were studied. As described below, the level of heat-induced apoptosis directly correlated with the duration of JNK activity following heat shock rather than with initial JNK activation. Constitutively expressed Hsp72 strongly reduced the duration of JNK activity, while it did not suppress initial JNK activation. These effects were due to Hsp72—mediated acceleration of JNK dephosphorylation, Inhibition of the effect of Hsp72 on duration of JNK activity by addition of vanadate, an inhibitor of JNK phosphatase, completely reversed anti-apoptotic effect of Hsp72. Therefore, suppression of heat-induced apoptosis by Hsp72 could be fully accounted by its effects on JNK activation. In addition, it was demonstrated that C-terminal fragment of Hsp72 which lacks ATPase activity accelerated JNK dephosphorylation, reduced the duration of JNK activity and suppressed heat-induced apoptosis. Therefore, protein refolding activity is dispensable for the effects of Hsp72 on JNK and on apoptosis.

7.1. Materials and Methods

7.1.1. Cell Lines

Parental Rat-1 fibroblasts and their variants expressing Hsp72 (MVH) and CTF (MVHΔBgl) were kindly provided by Dr. G. C. Li (Sloan Kettering). Cells were grown in DMEM supplemented with 10% fetal bovine serum and used for experiments at 40–70% confluence.

7.1.2. Adenoviral-based Expression of Hsp72 and SEK(K/R)

A recombinant adenovirus vector expressing Hsp72 (ADTR5Hsp72–GFP) was kindly provided by Dr. D. Mosser (Volloch, V., et al., 1998, Cell Stress & Chaperones 3: 265–271; Massie, B. et al., 1998, J. Virology 72(3): 2289–2296). Expression of this transcription unit is controlled by the tetracycline-regulated transactivator protein tTA. (Mosser, D. D, et al., 1997, Biotechniques 22(1): 150–16), which was expressed from the separate recombinant adenovirus (ADCMVTTA: Massie, B. et al., 1998, J. Virology 72(3): 2289–2296). Recombinant adenoviruses were generated by standard techniques as detailed by Jani, A. et al., (1997, J. Virological Methods 64(2): 111–124). Inoculation of cells with $3 \times 10^7$ pfu of each virus per 35 mm dish was sufficient to infect almost 100% of cells. This was confirmed each time by observation under a fluorescent microscope of a proportion of the cells expressing GFP.

SEK-1 (K/R) recombinant adenovirus was described previously Choukroun, G. et al., (1998, J. Clin. Invest. 102: 1311–1320). This construct expresses the kinase-inactive mutant of SEK-1 tagged with M2 FLAG epitope at its amino terminus (Choukroun, G. et al., 1998, J. Clin. Invest. 102: 1311–1320). Adenovirus was propagated in 293 cells and high titer stocks were obtained and purified by CsCl density gradient centrifugation.

7.1.3. Apoptosis Quantification and Measurement of JNK Activity

The level of apoptosis was measured by fluorescent microscopy using Hoechst-33342 DNA-specific dye (10 $\mu$M). Shrinked cells with condensed or fragmented nuclei were counted as apoptotic. Cells were washed twice with PBS on a dish, aspirated and lysed by thoroughly scraping with a plastic scraper in 200 $\mu$L lysis buffer per a 35 mm dish (40 mM HEPES, pH 7.5; 50 mM KCl; % TritonX100; 2 mM DTT, 1 mM $Na_3VO_4$; 50 mM $\beta$-glycerophosphate; 50 mM NaF; 5 mM EDTA; 5 mM EGTA; 1 mM PMSF; 1 mM benzamedine; 5 $\mu$g/ml of each: leupeptine, pepstatine A, aprotenin). The lysates were clarified by centrifugation in a microcentrifuge at 15,000 rpm for 5 min. Total protein concentration was measured in the supernatants after which they were diluted with the lysis buffer to achieve equivalent concentration in all samples. All procedures were performed at 4° C.

To measure JNK activity, 5 mL of extracts were added to a reaction mixture (20 ml final volume), containing (final concentration): 40 mM HEPES, pH 7.5; 1 mM $Na_3VO_4$; 25 mM $\beta$-glycerophosphate; 10 mM $MgCl_2$; 20 mM ATP; 15 $\mu$Ci of $^{32}$P-$\gamma$-ATP and 40 ng of recombinant c-Jun-GST. The reaction was allowed to proceed for 25 min at 30° C. and then was stopped by addition of 10 $\mu$L of loading SDS-PAGE buffer. Samples were separated by SDS-PAGE, transferred to nitrocellulose and membranes exposed to a Molecular Imager for quantitation. Subsequently, membranes were immunoblotted with JNK1 antibody to verify equivalent protein loading.

Another assay for JNK activity allowed us to measure separately activity of two major isoforms (46 kDa JNK1 and 54 kDa JNK2) using JNK antibody specific to activated (phosphorylated) form of JNK (Promega, Wis.). For immunoblot analysis samples were subjected to Western immunoblotting. Secondary antibodies conjugated with peroxidase were visualized with ECL substrates (Amersham, Arlington Heights, Ill.) and resulting films were quantified by densitometry. Measurement of JNK phosphatase activity. In vivo INK phosphatase activity was measured as described earlier (Meriin, A. B., et al., 1999, Mol. Cell Biol. (In press)). Briefly, cells were exposed to heat shock (45° C. for 30 min.) And transferred back to 37° C. Then further JNK phosphorylation (activation) was completely inhibited by addition 10 mM of 2-deoxyglucose and 5 $\mu$M of rotenone which rapidly deplete ATP, and cell samples were taken at different time points. The rate of JNK dephosphorylation was assessed under these conditions by immunoblotting with antibody which recognizes the activated (phosphorylated) form of JNK specifically.

7.2. Results

Constitutive expression of Hsp72 in Rat-1 fibroblasts blocks heat-induced apoptosis but does not affect initial activation of JNK. It has been demonstrated that transient expression of Hsp72 in cells exposed to heat shock leads to dramatic suppression of JNK activation which can account for the protective (anti-apoptotic) effect of Hsp72. Constitutive expression of this heat shock protein in some cell lines did not suppress JNK activation following a heat shock, but nevertheless, rendered cells thermoresistant (Buzzard, K. A., et al., 1998, J. Biol. Chem. 273: 17147–17153; Mosser, D. D., et al., 1997, Mol. Cell Biol. 17(9): 5317–5327). To address the mechanism underlying such thermoresistance, Rat-1 cells and a variant which constitutively expresses Hsp72 (MVH) were subjected to severe heat shock (45° C. 50 min). About 80% of the parental Rat-1 cells underwent apoptosis within 24 hours, while upon exposure of MVH cells to the same heat shock, the extent of apoptosis was only about 30% (FIG. 6B). Unexpectedly, when JNK activity was measured in these cells, similar levels of JNK activation were seen in parental Rat-1 and MVH cells (FIGS. 6C–D).

The above results suggested that heat-induced apoptosis may be JNK-independent in Rat-1 cells, which, would be in contrast to the observations with several other cell lines where heat-induced apoptosis was shown to be JNK-dependent (Zanke, B. W., et al., 1996, Current Biology 6(5): 606–613; Verheij, M. et al., 1996, Nature 380(6569): 75–79; Meriin, A. B., et al., 1999, Mol. Cell Biol. (In). To test this possibility, JNK activity was suppressed by expression of a dominant-interfering mutant form of JNK-activating kinase SEK1, SEK1(K/R). SEK1(K/R) has been successfully used by several groups to abolish activation of JNK by various stresses and cytokines and to demonstrate JNK-dependence of apoptosis in many cell lines (see e.g. ref Sanchez, I. Hughes et al., 1994, Nature 372(6508): 794–798; Verheij, M. et al., 1996, Nature 380(6569): 75–79; Meriin, A, et al., 1998, J. Biol. Chem. 273: 6373–6379). To express SEK1 (K/R) in Rat-1 cells an adenovirus-based system was used (Chokron, G. et al., 1998, J Clin Invest 102:1311–1320). The increasing amounts of viral particles were added to cell cultures and three days after infection, cells accumulated substantial amounts of SEK(K/R) protein, which directly correlated with the amount of adenovirus used for infection (FIG. 7). Heat-induced JNK activation was progressively suppressed in these cells and so was a heat-induced apoptosis (FIG. 7). Therefore, as with other tested cell lines, in Rat-1 cells JNK activity is a required component of heat-induced apoptotic pathway.

Since JNK is necessary for heat-induced apoptosis in Rat-1 cells, two possibilities exist; first, additional target(s) for Hsp72, beside JNK, exists within the heat-activated apoptotic pathway in this cellular model, or second, constitutively expressed Hsp72 influences the cell's viability not via the reduction of the extent of the initial JNK activation but by limitation of the duration of heat-induced JNK activity. The later possibility is consistent with several recent studies which suggested that a transient JNK activation is insufficient for the commitment to apoptosis induced by certain stimuli including gamma-radiation (Chen, Y. R. et al., 1996, J. Biol. Chem. 271(50): 31929–31936), TNF (Guo, Y. L., 1998, J. Biol. Chemi. 273: 4027–4034) and cisplatinum (Sanchez-Perez, I. et al., 1998, 16: 533–540), and only a prolonged activation of JNK following these treatments leads to apoptosis. Thus, it was tested whether heat-induced apoptosis in Rat-1 cells correlates with the duration of JNK activation.

Treatments of Rat-1 cells at 45° C. for 20, 30 or 50 min caused strong activation of JNK. Upon transfer of cells to 37° C., JNK activity increased further for at least an additional 1 hour, followed by the subsequent decline (FIG. 8A). While the extent of initial JNK activation induced by these heat treatments were almost identical, the rates of the decline of JNK activity differed dramatically. In cells exposed to 45° C. for 20 min., JNK activity fell to 50% of its maximal level within 2.5 h after heat shock, whereas in cells heat-shocked for 30 min JNK activity declined to 50% of its maximal level only after 4 hrs. After a more severe heat treatment (45° C. for 50 min), JNK activity remained close to its maximal level for more than 5 h after transfer to normal temperature. When assessed after 8 hrs, neither 2-min nor 30-min heat treatments induced apoptosis, whereas in culture treated for 50 min 40% of cells were apoptotic. When measured after 24 hrs, no apoptosis was observed after 20-min heat treatment, and rather minor fractions of cells became apoptotic in cultures heat-shocked for 30 min (about 30%), whereas 50 min treatment caused apoptosis in 80% of cells (FIG. 8B). Hence, the onset and the extent of heat-induced apoptosis in Rat-1 cells correlates with the duration of JNK activation rather then with the extent of the initial JNK activation following heat shock.

The results described above indicate that in protecting against heat-induced apoptosis, Hsp72 facilitates (directly or indirectly) JNK inactivation. Indeed, upon both mild (30 min at 45° C.) and severe (50 min at 45° C.) heat shock, JNK inactivation in Hsp72-expressing cells occurred significantly faster than in parental cells (FIGS. 9A–B). While, as mentioned above, in paternal cells JNK activity remained very close to its maximal level 5 hrs after the 50-min heat shock (projected time for decline to 50% level was about 14 hrs) (FIG. 9B), in MVH cells JNK activity fell to 50% of its maximal level 4 h after heat shock. Therefore, Hsp72 accelerated the decline of JNK activity, so that the rate of JNK inactivation in Hsp72-expressing cells after severe heat shock (50 min at 45° C.) resembled that seen in parental cells after milder heat shock (30 min at 45° C.) (FIG. 9B). The extent of apoptosis in so treated MVH cells was only 35%, also similar to that seen in parental cells exposed to milder heat shock (30 min at 45° C.) (FIG. 9B). Thus, Hsp72-mediated protection against apoptosis (FIG. 6B) correlates well with tile rate of JNK inactivation (FIG. 9B).

UV-irradiation, osmotic stress and cytokines activate JNK via phosphorylation by the dual specificity kinases SEK1 and MKK7 (Sanchez, I. Hughes et al., 1994, Nature 372 (6508): 794–798; Ganiatsas, S. et al., 1998, Proc. Natl. Acad. Sci. USA 95: 6881–6886; Finch, a. et al., 1997, Febs. Lett. 418:144–14). In contrast, the data described herein demonstrates that heat shock and other protein damaging stresses do not facilitate JNK phosphorylation but rather inhibit its dephosphorylation, thus leading to increase in JNK activity (Meriin, A. B., et al., 1999, Mol. Cell biol. (In press)). The later stresses do not affect the activity of SEK1, which remains at its basal level. In unstressed cells, when JNK phosphatase is active, the basal SEK1 activity is insufficient to maintain the high level of phosphorylated JNK, whereas after heat shock, when JNK phosphatase is suppressed, the basal SEK1 activity is sufficient to support the increase in the level of active JNK. The suppression of basal SEK1 activity by either SEK1 gene knockout or by expression of dominant-interfering SEK1 (K/R) mutant prevents activation of JNK by heat shock (Meriin, A, et al., 1998, J. Biol. Chem. 273: 6373–6379; Ganiatsas, S. et al., 1998, Proc. Natl. Acad. Sci. USA 95: 6881–6886). Transient induction of Hsp72 suppresses the inhibitory effect of heat shock on JNK dephosphorylation (Meriin, A. B., et al., 1999, Mol. Cell biol. (In press)). Based on these observations, experiments were conducted to test if stable expression of Hsp72 accelerates the inactivation of JNK following severe heat shock by facilitating JNK phosphatase(s) activity. To assess the activity of JNK phosphatase(s), the rate of JNK dephosphorylation was measured under the conditions when upstream JNK-activating kinases are completely suppressed (Meriin, A. B., et al., 1999, Mol. Cell biol. (In). Using this approach, it was observed that, in parental Rat-1 cells following heat shock, JNK phosphatase(s) activity sharply declines, thus accounting for the heat-induced activation of JNK (FIG. 10A). However, in heat-stressed cells expressing Hsp72, the activity of JNK phosphatase(s) was about 3-times higher than that of parental heat-stressed cells (FIG. 10A). On the other hand, heat shock did not activate SEK1 either in parental or in MVH cells. Thus, Hsp72 accelerates JNK inactivation by facilitating the increase in the activity of JNK phosphatase(s) in heat-shocked Rat-1 cells. Given these results a model can be set forth in which accelerated JNK inactivation fully accounts for the anti-apoptotic effect of Hsp72. Such a model implies a straightforward and readily testable prediction that the prevention of JNK inactivation via inhibition of its phosphatase(s) in Hsp72-expressing cells should decrease or abolish their thermoresistance.

To inhibit JNK phosphatase(s), ortho-vanadate, a well-known general phosphatase inhibitor was used. Ortho-vanadate effectively suppresses JNK phosphatase(s) in various cell lines (Meriin, A. B., et al., 1999, Mol. Cell biol. (In press); Chen, Y. R. et al., 1996, J. Biol. Chem. 271(50): 31929–31936; Guo, Y. L., 1998, J. Biol. Chemi. 273: 4027–4034). Treatment of unstressed cells with vanadate alone affected neither JNK activity nor the proportion of apoptopic cells. On the other hand, when added 1 hour after the stress, ortho-vanadate strongly inhibited JNK inactivation in heat-shocked MVH cells (FIGS. 11A,B). At the time, vanadate dramatically increased heat-induced (50 min at 45° C.) apoptosis of MVH cells (FIG. 11C). Therefore, inhibition of JNK phosphatase(s) and prolongation of JNK activation in heat-shocked Hsp72-expressing cells abolishes their thermoresistance, indicating that the accelerated JNK inactivation indeed accounts for the resistance to apoptosis in Rat-1 cells constitutively expressing Hsp72. The effects of transient expression of recombinant Hsp72 on JNK activation in Rat-1 cells was studied to determine whether a cellular adaptation which alters the regulation of JNK activity in response to stress occurs. Transient expression of Hsp72 was achieved by infection with an adenoviral construct encoding Hsp72 under the control of a tetracycline-inhabitable transactivator. When infected Rat-1 cells where challenged with a heat shock (45° C., 30 min), no suppression of the initial JNK activation was observed but, as with constitutively expressed Hsp72, JNK inactivation was accelerated (FIG. 12). In another approach, transient expression of Hsp72 (and other heat shock proteins) was achieved by pretreatment of Rat-1 with mild heat shock (45° C. for 15 min) followed by 16 hours of recovery. Such pretreatment made cells thermotolerant so that apoptosis in response to severe heat shock (45° C., 50 min) was reduced by more than 3-fold (FIG. 13A). As was seen with constitutively and transiently expressed recombinant Hsp72 (see FIGS. 9, 12), pretreatment with mild heat shock did not reduce the initial level of heat-induced JNK activation but accelerated JNK inactivation (FIG. 13B). Therefore, in Rat-1 cells transient and constitutive expression of Hsp72 have similar effects: both affect the rate of JNK inactivation without suppressing the extent of the initial JNK activation. Furthermore, as with constitutive expression of Hsp72 in MVH cells, induced expression of this heat shock protein in parental cells pretreated with mild heat shock was resulted from acceleration of JNK dephosphorylation (see FIG. 10 above). Therefore, the dissimilarity in effects of Hsp72 on heat-induced JNK activity in these and prior experiments could either be due to the variance in experimental conditions, e.g. differences in cellular levels of Hsp72 and in the severity of heat shock, or to the differences in cell lines.

To distinguish between these possibilities, two approaches were pursued. In the first approach MVH30 cells were utilized. A clone was selected that expresses Hsp72 at significantly higher level than MVH cells (FIG. 14A). Rat-1 cells, MVH cells and MVH30 cells were treated for 30 min at 45° C., and JNK activity was measured. As shown in FIG. 14B, whereas the extent of the initial JNK activation was practically identical for Rat-1 and MVH cells, it was three fold lower in MVH30 cells. In the second approach the effect of Hsp72 on the initial JNK activation following less severe heat shock was assessed. MVH cells as well as naive and preheated parental Rat-1 cells were challenged with a relatively mild heat shock (43° C., 30 min), and JNK activity was measured immediately after the challenge. As seen in FIG. 14C, the initial activation of JNK under these conditions was suppressed in both preheated and Hsp72-expressing cells.

Thus, upon relatively mild heat shock conditions, Hsp72, expressed either transiently or constitutively, is capable of suppression of the initial heat-induced JNK activation. Upon severe heat shock, however, the ability of Hsp72 to suppress the initial JNK activation depends on its cellular level. When this level is not sufficiently high, Hsp72 loses its ability to suppress the initial JNK activation independently of the manner of expression but is still able to accelerate JNK inactivation. The C-terminal fragment (CTF) of Hsp72 contains the peptide binding domain but lacks ATPase activity. Accordingly, it can bind to damaged proteins but cannot dissociate from them, and therefore cannot refold them. However, like constitutive expression of Hsp72, expression of CTF (called ΔBgl in ref. Li, G. C., et al, 1992, Proc. Natl. Acad. Sci. USA 89: 2036–2040) was shown to protect Rat-1 cells from heat shock, as measured by the retention of cell's colony forming ability following heat treatment (Li, G. C., et al, 1992, Proc. Natl. Acad. Sci. USA 89: 2036–2040). Such protection is reminiscent of the protective effect of Hsp72. This similarity raises the possibility that, like Hsp72, CTF can suppress inhibition of JNK dephosphorylation in heat-shocked cells, and, as a result, can protect from heat-induced apoptosis.

Figure 15A:
Figure 15A:
Figure 15B:
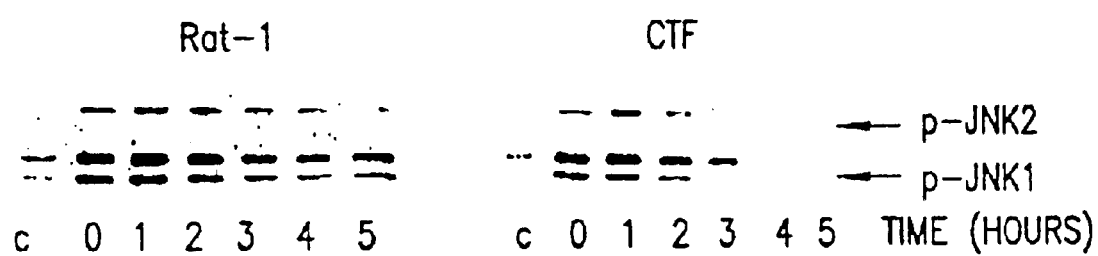
Figure 15C:
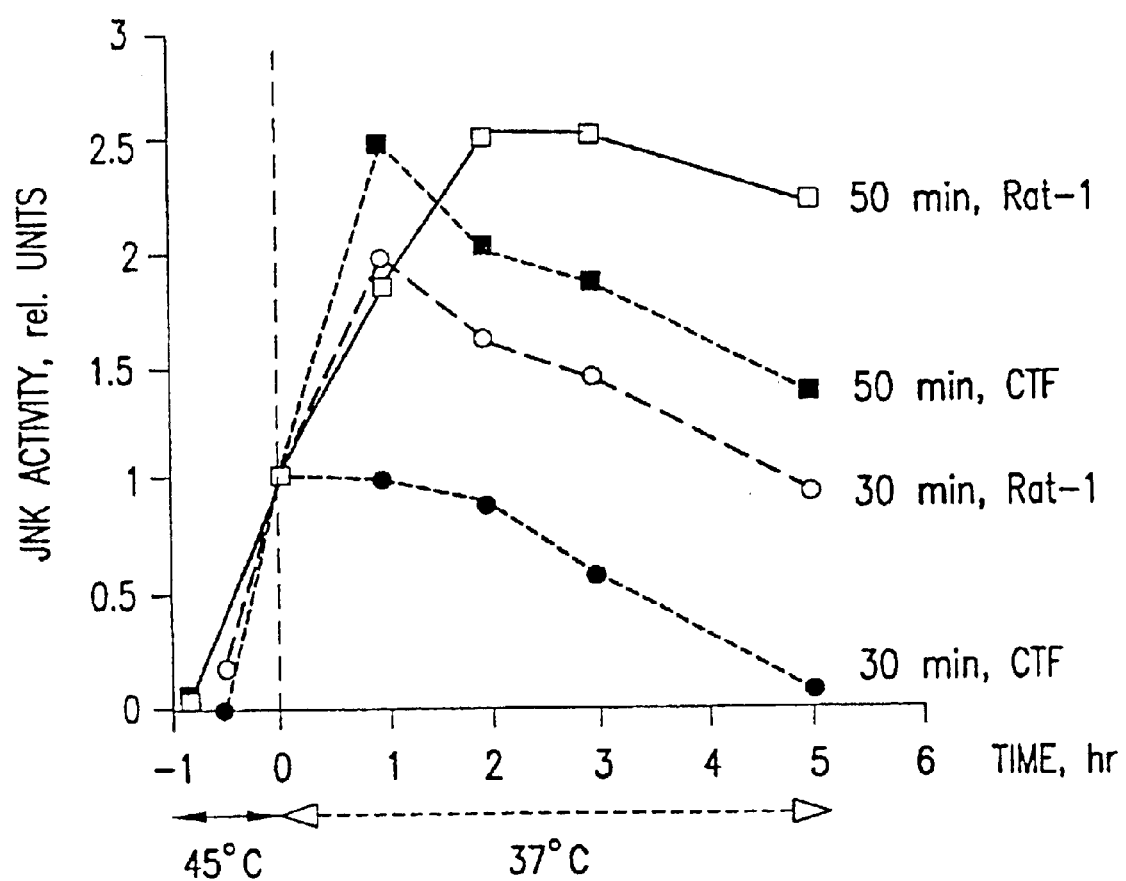
Figure 15D:
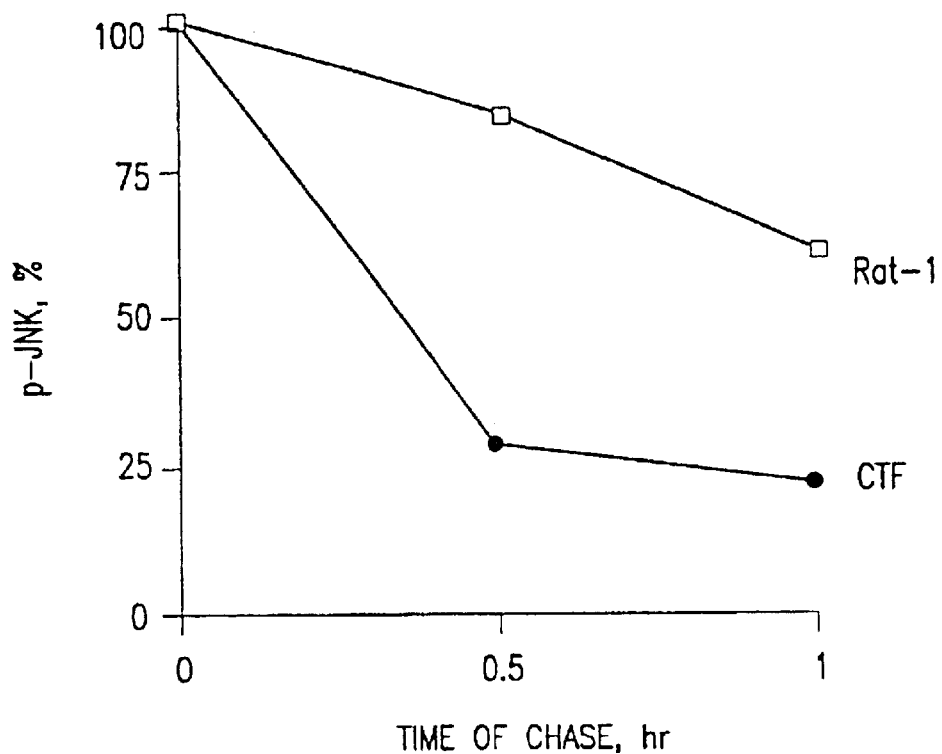
Figure 15E:
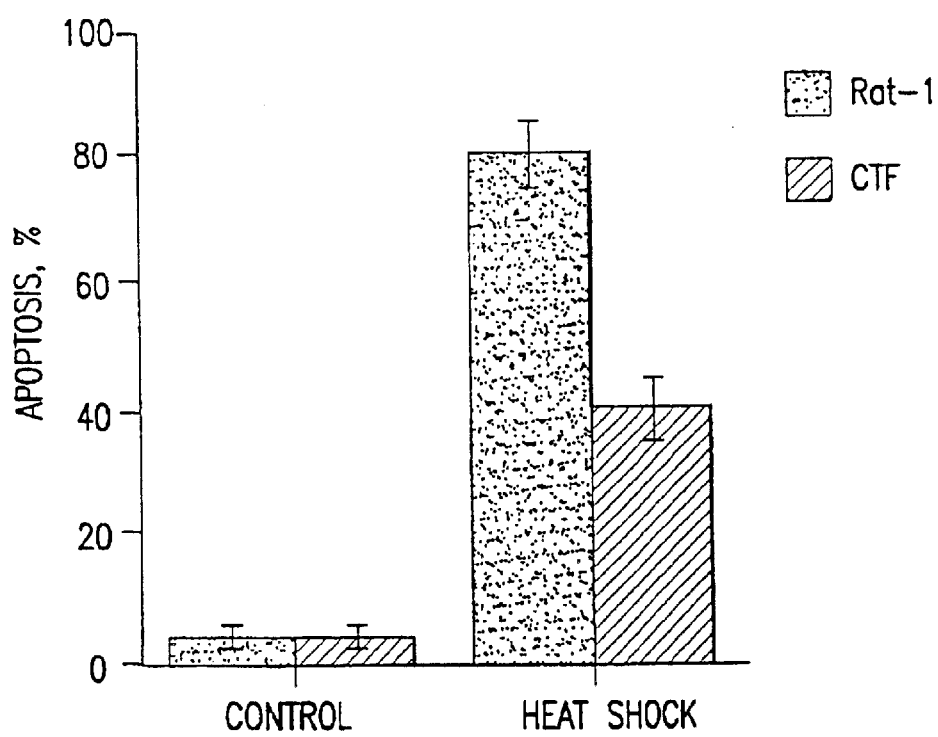

The effects of CTF expression on the rate of JNK inactivation was measured following heat shock. It was observed that similarly to Hsp72-expressing cells, whereas CTF did not suppress the initial extent of JNK activation following heat shock, JNK inactivation in CTF-expressing cells occurred significantly faster than in parental cells. In fact, the level of JNK activity fell to 50% of maximum, 5 hours after heat shock in CTF-expressing cells versus projected 14 hours in parental cells (FIG. 15B). To test whether the mechanism underlying the observed acceleration of JNK inactivation by CTF is the same as seen with Hsp72 CTF-expressing cells were challenged with severe heat shock (45° C. for 50 min), followed by measurement of the rate of JNK dephosphorylation following ATP depletion as described above. As seen in FIG. 15C, in heat shocked CTF-expressing cells, the rate of JNK dephosphorylation was at least three times faster than that in control cells. Thus, an Hsp72 mutant, which lacks ATPase and protein refolding activities, can accelerate JNK inactivation following heat shock by facilitating JNK dephosphorylation. Acceleration of JNK inactivation by CTF was sufficient for significant protection against heat-induced apoptosis. Indeed, the extent of apoptosis in CTF-expressing cells exposed to heat shock at 45° C. for 50 min was by more than 50% lower than that in parental cells under similar conditions (FIG. 15D). The above data, demonstrates that the potential of Hsp72 to suppress heat-induced JNK activation and prevent apoptosis is confined in its peptide binding domain, whereas protein refolding activity of Hsp72 appears to be irrelevant to these effects.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims. Various references are cited herein, the disclosures of which are incorporated by reference in their entireties.

What is claimed is:

1. A method for identifying compounds that inhibit cell proliferation comprising:
   (a) contacting a heat shock 72 kD protein and a test compound under conditions and for a sufficient time to allow the two components to interact and bind, thus forming a complex;
   (b) detecting the formation of a complex; and
   (c) determining whether a test compound, found to interact and bind to the heat shock 72 kD protein, is capable of inhibiting cell proliferation.

2. The method of claim 1 wherein the heat shock 72 kD protein is the C-terminal peptide binding domain.

3. The method of claim 1 or 2 in which the ability to inhibit all cell proliferation is determined by measuring the level of anchorage-independent cell growth.

4. The method of claim 1 or 2 in which the ability to inhibit all cell proliferation is determined by measuring the level of cell growth in soft agar.

5. The method of claim 1 or 2 in which the ability to inhibit all cell proliferation is determined by measuring the level of heat shock induced apoptosis.

* * * * *

SEQUENCE LISTING

<160> NUMBER OF SEQ ID NOS: 2

<210> SEQ ID NO 1
<211> LENGTH: 2700
<212> TYPE: DNA
<213> ORGANISM: Homo sapien

<400> SEQUENCE: 1

```
cgccatggag cctccagtga tgattggtcc acctggcagc cgacttataa gacagtccac      60
ctgtgcggct tcgcggatcc ggaaccggca gtgggggtgt accccagct caggtggcgc     120 ttcggcgacc ggagacaagc gagatctcgt ccggtgacca accaacaccc atcccagaag     180
aaggaaggct ctcatcgagc aacgccaggg tacctttttc gcaggcaccg agtgttccgt     240
tggccaaagc tccaacacgg acgtggcctt tgaacccgca cggtggtgca ccaaggtgca     300
ccatggtgct acgcggtgat ttcccaccgc actctggaga gggggcagg tcggtgattg     360 gcaagcggtc gagagtgact gcgcgtcgag ttccagcccc cgcggcgatc caaggtggag     420
cacggacacc gaacaccgtg gtcggacatg ggtgagctac gaccaagatg caccgtgccg     480
```

```
cactccccct gttctgagca acgggaggcg gctcagaagg cggataacgg cccgttgtcc      540
tttccggcgt caatctcaga ggcatcgacc atcatcgcca gagcggctca tttgacgcga      600
aagcactggc aagggggaga aaggagatcg gcctacttca tcctctcagg ggggcggca       660 aaaccctgg gaaaaggcgg ctagcctgag caaggcttcc ccggaaggac gcggagccga       720
tgggcaccac acgaccaggg tcggggatgc agcgcctgat cttccaggt ccaaggcatt       780 ccgaggcgta acgactcgca gtccctgtcc ctctggcctc aatattcccg gtctccgtga      840
gagctgctgc cagagcgaac cgagctcttc cagagagcag ctactcctgc caaccgcacc      900
ggccaagaac tggccgcaag atcaacgac ctaccccgag cctgggctac gcgccaggcc       960
accaaggatg ccgccgcca tttgacctgg gaggtgaagg gtgaaccact cgagccgtga       1020
acccaggcca accagggcga gagaaggctc ggggctcca gacctgaaca gccatcctga       1080
cccctgtcgc tccaccatcc gtgctgatcc cgcttcgagc ttcgacatcg ccaacaaga       1140 atggtgcagg gccaagaacg ctcaagggca atctcgtggc gagctggagc gggcctgggg      1200
gaggaggtag tgcatttcct tttttggtga tactgccatc ttggttactt cgggtgtgat      1260
tcgcctacgg gcgggggcac ccacggccgg tcgtggagga ggcggctgcg gcctggagat      1320
ggttcgagga tgcgcgacgc cccgcatccc agagcatcaa tggggggacaa tggggctgga     1380 ccaccaagca aggtgtacga tgagcggcat atgccaacgg tcaccatcac aggcggagaa     1440
ccctggagtc agatcagcga tggacgccaa aggtgtgtaa gcttcggggc attaggggcc     1500
agtatttctg agtactgaac ttacgactat caaagtaaat cgcggggctc cctggacaga     1560
cttcgacgtg ggacacccac gttcaagaga caccgcctgc cgactccctg gctgtgctcc     1620
caagctggac caaggtgcag ccccgacgag gtccgagaac gacggccgga gacgcagatc     1680
gggcgagagg ccctccggcc catcctgaac caacgacaag gtacaaagcg ctacgccttc     1740
ggccgacaag caccttggcc ccccatcatc tcagggtccc tttccaagat tttgtcagtt     1800 ttgcctttt ttcttctttt aaactttaaa aacgtgctgc acgggcaagg tccatcctga     1860
ctgggtgggg aaaacacaaga gagagggcca tttgagggca gacctgttcc aaggcccaga     1920
aagctgctgc gctgtggcct gtgcaggacc ggcgtgatga ttcaccacct gccatgacga     1980
cccaggggcg gtcacggcca ggccgcctga gaggacgagg aacatgaaga aagaaggtgc     2040
gagaaggacg agcggactgt aagggagggt tgctgttttt ctcaatttcc ttccggtttc     2100
taatacactt attcaagtga ggatcatcaa gggagcgcaa cgatcgacga aggactttga     2160
aggacatcag agaggaccct tcgacttcta gaagcaccct ttcacgacct aggacttctt     2220
acggggcggc tgctgctgct ctgccctgat actccgacaa aagacaacaa tgccccagat     2280
cggacaagag gcaaggagga tgcagcgcga gcgccgtgga tggacaagtg agtttgagca     2340
accagggtgc ctgggtcagg gttttggagc tgtgtttgca tacatgcaga aactcaggcc     2400
tgccctttta cgagcccacg cgtgctcatc cggcatcttc caacaggctg ccagaacaag     2460
gtcgtccagc cacgtccatc ggagcccgtg gtcctggtc aacgggcgc ggtgcaggcg      2520 ggacgtggct caagcgcaac ccaacccggg tctgttgggg cgaggtgacc caccggcaag     2580
gatcgagcgc gagggtgtca ggatgagggg tcaagaggtc caagaggaag cggtggtccc     2640
ccccaccatt tcaagacttt atgttgaaat gatgaattta atttttaag ttcctttatt      2700
```

<210> SEQ ID NO 2
<211> LENGTH: 622
<212> TYPE: PRT
<213> ORGANISM: Homo sapien

<400> SEQUENCE: 2

```
Met Ala Lys Ala Ala Ala Ile Gly Ile Asp Leu Gly Thr Thr Tyr Ser
  1               5                  10                  15
Cys Val Gly Val Phe Gln His Gly Lys Val Glu Ile Ile Ala Asn Asp
                 20                  25                  30
Gln Gly Asn Arg Thr Thr Pro Ser Tyr Val Ala Phe Thr Asp Thr Glu
             35                  40                  45
Arg Leu Ile Gly Asp Ala Ala Lys Asn Gln Val Ala Leu Asn Pro Gln
 50                  55                  60
Asn Thr Val Phe Asp Ala Lys Arg Leu Ile Gly Arg Lys Phe Gly Asp
 65                  70                  75                  80
Pro Val Val Gln Ser Asp Met Lys His Trp Pro Phe Gln Val Ile Asn
                 85                  90                  95
Asp Gly Asp Lys Pro Lys Val Gln Val Ser Tyr Lys Gly Glu Thr Lys
                100                 105                 110
Ala Phe Tyr Pro Glu Glu Ile Ser Ser Met Val Leu Thr Lys Met Lys
            115                 120                 125
Glu Ile Ala Glu Ala Tyr Leu Gly Tyr Pro Val Thr Asn Ala Val Ile
130                 135                 140
Thr Val Pro Ala Tyr Phe Asn Asp Ser Gln Arg Gln Ala Thr Lys Asp
145                 150                 155                 160
Ala Gly Val Ile Ala Gly Leu Asn Val Leu Arg Ile Ile Asn Glu Pro
                165                 170                 175
Thr Ala Ala Ile Ala Tyr Gly Leu Asp Arg Thr Gly Lys Gly Glu
            180                 185                 190
Arg Asn Val Leu Ile Phe Asp Leu Gly Gly Gly Thr Phe Asp Val Ser
                195                 200                 205
Ile Leu Thr Ile Asp Asp Gly Ile Phe Glu Val Lys Ala Thr Ala Gly
210                 215                 220
Asp Thr His Leu Gly Gly Glu Asp Phe Asp Asn Arg Val Asn His Phe
225                 230                 235                 240
Val Glu Glu Phe Lys Arg Lys His Lys Lys Asp Ile Ser Gln Asn Lys
                245                 250                 255
Arg Ala Val Arg Arg Leu Arg Thr Ala Cys Glu Arg Ala Lys Arg Thr
                260                 265                 270
Leu Ser Ser Ser Thr Gln Ala Ser Leu Glu Ile Asp Ser Leu Phe Glu
            275                 280                 285
Gly Ile Asp Phe Tyr Thr Ser Ile Thr Arg Ala Arg Phe Glu Glu Leu
290                 295                 300
Cys Ser Asp Leu Phe Arg Ser Thr Leu Glu Pro Val Glu Lys Ala Leu
305                 310                 315                 320
Arg Asp Ala Lys Leu Asp Lys Ala Gln Ile His Asp Leu Val Leu Val
                325                 330                 335
Gly Gly Ser Thr Arg Ile Pro Lys Val Gln Lys Leu Leu Gln Phe Phe
                340                 345                 350
Asn Gly Arg Asp Leu Asn Lys Ser Ile Asn Pro Asp Glu Ala Val Ala
            355                 360                 365
Tyr Gly Ala Ala Val Gln Ala Ala Ile Leu Met Gly Asp Lys Ser Glu
370                 375                 380
Asn Val Gln Asp Leu Leu Leu Leu Asp Val Ala Pro Leu Ser Leu Gly
385                 390                 395                 400
Leu Glu Thr Ala Gly Gly Val Met Thr Ala Leu Ile Lys Arg Asn Ser
                405                 410                 415
```

```
                                    -continued
Thr Ile Pro Thr Lys Gln Thr Gln Ile Phe Thr Thr Tyr Ser Asp Asn
            420             425             430

Gln Pro Gly Val Leu Ile Gln Val Tyr Glu Gly Glu Arg Ala Met Thr
        435             440             445

Lys Asp Asn Asn Leu Leu Gly Arg Phe Glu Leu Ser Gly Ile Pro Pro
    450             455             460

Ala Pro Arg Gly Val Pro Gln Ile Glu Val Thr Phe Asp Ile Asp Ala
465             470             475             480

Asn Gly Ile Leu Asn Val Thr Ala Thr Asp Lys Ser Thr Gly Lys Ala
            485             490             495

Asn Lys Ile Thr Ile Thr Asn Asp Lys Gly Arg Leu Ser Lys Glu Glu
            500             505             510

Ile Glu Arg Met Val Gln Glu Ala Glu Lys Tyr Lys Ala Glu Asp Glu
            515             520             525

Val Gln Arg Glu Arg Val Ser Ala Lys Asn Ala Leu Glu Ser Tyr Ala
        530             535             540

Phe Asn Met Lys Ser Ala Val Glu Asp Glu Gly Leu Lys Gly Lys Ile
545             550             555             560

Ser Glu Ala Asp Lys Lys Lys Val Leu Asp Lys Cys Gln Glu Val Ile
            565             570             575

Ser Trp Leu Asp Ala Asn Thr Leu Ala Glu Lys Asp Glu Phe Glu His
            580             585             590

Lys Arg Lys Glu Leu Glu Gln Val Cys Asn Pro Ile Ile Ser Gly Leu
        595             600             605

Tyr Gln Gly Ala Gly Gly Pro Gly Pro Gly Gly Phe Gly Ala
    610             615             620
```